(12) United States Patent
Ilg et al.

(10) Patent No.: US 8,530,381 B2
(45) Date of Patent: Sep. 10, 2013

(54) ACTIVE COMPOUND COMBINATIONS

(75) Inventors: Kerstin Ilg, Köln (DE); Ulrich Heinemann, Leichlingen (DE); Peter Dahmen, Neuss (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 370 days.

(21) Appl. No.: 12/969,694

(22) Filed: Dec. 16, 2010

(65) Prior Publication Data

US 2011/0152077 A1    Jun. 23, 2011

Related U.S. Application Data

(60) Provisional application No. 61/287,475, filed on Dec. 17, 2009.

(30) Foreign Application Priority Data

Dec. 16, 2009    (EP) .................................... 09179444

(51) Int. Cl.

| | | |
|---|---|---|
| *A01N 43/836* | (2006.01) | |
| *A01N 43/84* | (2006.01) | |
| *A01N 37/50* | (2006.01) | |
| *A01N 43/56* | (2006.01) | |
| *A01N 43/653* | (2006.01) | |
| *A01N 55/10* | (2006.01) | |
| *A01P 3/00* | (2006.01) | |

(52) U.S. Cl.
USPC .......... 504/100; 514/63; 514/236.2; 514/326; 514/361; 514/384; 514/406; 514/422; 514/539

(58) Field of Classification Search
USPC ................ 504/100; 514/63, 236.2, 326, 361, 514/384, 406, 422, 539
See application file for complete search history.

(56) References Cited

U.S. PATENT DOCUMENTS

| | | | | |
|---|---|---|---|---|
| 8,383,139 | B2 * | 2/2013 | Kunz et al. .................... | 424/405 |
| 2004/0241098 | A1 | 12/2004 | Labourdette et al. | |
| 2009/0247551 | A1 | 10/2009 | Jeschke et al. | |
| 2009/0253749 | A1 | 10/2009 | Jeschke et al. | |
| 2010/0240705 | A1 | 9/2010 | Jeschke et al. | |
| 2011/0143937 | A1 * | 6/2011 | Kunz et al. .................... | 504/100 |

FOREIGN PATENT DOCUMENTS

| | | |
|---|---|---|
| CA | 2 729 432 A1 | 12/2009 |
| EP | 0 539 588 A1 | 5/1993 |
| WO | WO 89/10396 A1 | 11/1989 |
| WO | WO 00/46184 A1 | 8/2000 |
| WO | WO 02/12172 A1 | 2/2002 |
| WO | WO 03/024219 A1 | 3/2003 |
| WO | WO 03/093224 A1 | 11/2003 |
| WO | WO 2004/058723 A1 | 7/2004 |
| WO | WO 2005/089547 A1 | 9/2005 |
| WO | WO 2005/120234 A2 | 12/2005 |
| WO | WO 2007/024782 A2 | 3/2007 |
| WO | WO 2007/031507 A1 | 3/2007 |
| WO | WO 2007/149134 A1 | 12/2007 |
| WO | WO 2009/156098 | * 12/2009 |

OTHER PUBLICATIONS

Bauer, T.A., et al., "Response of Selected Weed Species to Postemergence Imazethapyr and Bentazon," *Weed Tech.* 9:236-242, The Weed Science Society of America (1995).
Blackshaw, R.E., "HOE-39866 Use in Chemical Fallow Systems," *Weed Tech.* 3:420-428, The Weed Science Society of America (1989).
Blackshaw, R.E., "Synergistic Mixes of DPX-A7881 and Clopyralid in Canola (*Brassica napus*)," *Weed Tech.* 3:690-695, The Weed Science Society of America (1989).
Blackshaw, R.E., et al., "Herbicide Combinations for Postemergent Weed Control in Safflower (*Carthamus tinctorius*)," *Weed Tech.* 4:97-104, The Weed Science Society of America (1990).
Blouin, D.C., et al., "Analysis of Synergistic and Antagonistic Effects of Herbicides Using Nonlinear Mixed-Model Methodology," *Weed Tech.* 18:464-472, The Weed Science Society of America (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America (2000).
Buker, III, R.S., et al., "Confirmation and Control of a Paraquat-Tolerant Goosegrass (*Eleusine indica*) Biotype," *Weed Tech.* 16:309-313, The Weed Science Society of America (2002).
Burke, I.C., et al., "CGA-362622 Antagonizes Annual Grass Control with Clethodim," *Weed Tech.* 16:749-754, The Weed Science Society of America (2002).
Colby, S.R., "Calculating Synergistic and Antagonistic Responses of Herbicide Combinations," *Weeds* 15:20-22, Weed Science Society of America (1967).
Crickmore, N., et al., "Revision of the Nomenclature for *Bacillus thuringiensis* Pesticidal Crystal Proteins", *Microbiology and Molecular Biology Reviews* 62:807-813, American Society for Microbiology, United States (1998).
Flint, J.L., et al., "Analyzing Herbicide Interactions, A Statistical Treatment of Colby's Method," *Weed Tech.* 2:304-309, The Weed Science Society of America (1988).

(Continued)

*Primary Examiner* — John Pak
(74) *Attorney, Agent, or Firm* — Sterne, Kessler, Goldstein & Fox P.L.L.C.

(57) ABSTRACT

The invention relates to active compound combinations, in particular within a composition, which comprises (A) an amidine compound of formula (I) and a further fungicidally (B-1), insecticidally (B-2) active or plant growth regulating compound (B-3). Moreover, the invention relates to a method for curatively or preventively controlling the phytopathogenic fungi of plants or reducing the mycotoxin contamination of plant or plant parts, to the use of a combination according to the invention for the treatment of seed, to a method for protecting a seed and not at least to the treated seed.

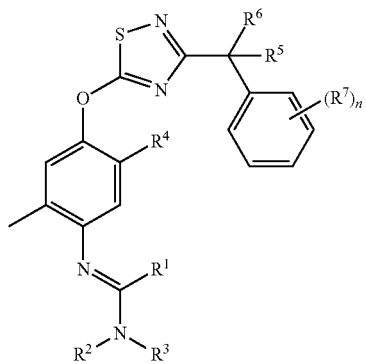

20 Claims, No Drawings

(56) References Cited

OTHER PUBLICATIONS

Gillespie, G.R., and Nalewaja, J.D., "Wheat (*Triticum aestivum*) Response to Triallate Plus Chlorsulfuron," *Weed Tech.* 3:20-23, The Weed Science Society of America (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America (1988).

Harker, K.N., and O'Sullivan, P.A., "Synergistic Mixtures of Sethoxydim and Fluazifop on Annual Grass Weeds," *Weed Tech.* 5:310-316, The Weed Science Society of America (1991).

Kent, L.M., et al., "Effect of Ammonium Sulfate, Imazapyr, and Environment on the Phytotoxicity of Imazethapyr," *Weed Tech.* 5:202-205, The Weed Science Society of America (1991).

Kotoula-Syka, E., et al., "Interactions Between SAN 582H and Selected Safeners on Grain Sorghum (*Sorghum bicolor*) and Corn (*Zea mays*)," *Weed Tech.* 10:299-304, The Weed Science Society of America (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America (2002).

Moreno, O.J. & Kang, M.S., "Aflatoxins in maize: The problem and genetic solutions," *Plant Breeding* 118:1-16, Blackwell Wissenschafts-Verlag, Berlin, Germany (1999).

Norris, J.L., et al., "Weed Control from Herbicide Combinations with Three Formulations of Glyphosate," *Weed Tech.* 15:552-558, The Weed Science Society of America (2001).

Novosel, K.M., et al., "Metolachlor Efficacy as Influenced by Three Acetolactate Synthase-Inhibiting Herbicides," *Weed Tech.* 12:248-253, The Weed Science Society of America (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America (2000).

Rummens, F.H.A., "An Improved Definition of Synergistic and Antagonistic Effects," *Weed Science* 23(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech.* 6:922-929, The Weed Science Society of America (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America (1998).

Shaw, D.R. and Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination with Pyrithiobac," *Weed Tech.* 10:889-892, The Weed Science Society of America (1996).

Sun, Y.-P. & Johnson, E.R., "Analysis of Joint Action of Insecticides Against House Flies", *J. Econ. Entomol.* 53:887-892, United States (1960).

Tammes, P.M.L., "Isoboles, A Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America (1997).

Zhang, W., et al., "Fenoxaprop Interactions for Barnyardgrass (*Echinochloa crus-galli*) Control in Rice," *Weed Tech.* 19:293-297, The Weed Science Society of America (2005).

European Search Report of European Application No. 09179444.6, mailed Jun. 7, 2010.

\* cited by examiner

ACTIVE COMPOUND COMBINATIONS

The invention relates to active compound combinations, in particular within a composition, which comprises (A) an amidine compound of formula (I) and a further fungicidally (B-1), insecticidally (B-2) active or plant growth regulating compound (B-3). Moreover, the invention relates to a method for curatively or preventively controlling the phytopathogenic fungi of plants or reducing the mycotoxin contamination of plant or plant parts, to the use of a combination according to the invention for the treatment of seed, to a method for protecting a seed and not at least to the treated seed.

WO-A-00/046 184 and WO-A-03/093 224 each disclose the use of arylamidines as fungicides.

WO-A-03/024 219, WO-A-05/089 547 and WO-A-05/120 234 each disclose fungicide combinations comprising at least one phenylamidine and at least one further known fungicidally active ingredient.

The unpublished international patent application PCT/EP/2009/004419 discloses thiadiazolyloxyphenylamidine compounds according to formula (I), methods for producing such compounds starting from commercially available ingredients and its fungicidal uses. The disclosure of this application shall be fully incorporated herein by reference.

In conjunction with the present invention, the term plant growth regulator (PGRs) denotes an active ingredient or a combination of such a.i.s, which influences germination, growth, maturation or development of plants or its fruits.

Since, moreover, the environmental and economic requirements imposed on modern-day fungicides are continually increasing, with regard, for example, to the spectrum of action, toxicity, selectivity, application rate, formation of residues, and favourable preparation ability, and since, furthermore, there may be problems, for example, with resistances, it is constant task to develop new fungicide agents which in some areas at least have advantages over their known counterparts.

The invention provides active compound combinations/compositions which in some aspects at least achieve the stated objectives.

It has now been found, surprisingly, that the combinations according to the invention not only bring about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the combination still achieves a high degree of phytopathogen control and reduction in mycotoxin contamination even where the two individual compounds have become totally ineffective in such a low application rate range. This allows, on the one hand, a substantial broadening of the spectrum of phytopathogens that can be controlled and, on the other hand, increased safety in use.

However, besides the actual synergistic action with respect to fungicidal and mycotoxin-reducing activity, the combinations according to the invention also have further surprising advantageous properties which can also be described, in a wider sense, as synergistic activity. Examples of such advantageous properties that may be mentioned are: a broadening of the spectrum of fungicidal activity to other phytopathogens, for example to resistant strains; a reduction in the rate of application of the active ingredients; adequate pest control with the aid of the compositions according to the invention, even at a rate of application at which the individual compounds are totally ineffective; advantageous behaviour during formulation or upon application, for example upon grinding, sieving, emulsifying, dissolving or dispensing; increased storage stability; improved stability to light; more advantageous degradability; improved toxicological or ecotoxicological behaviour; improved characteristics of the useful plants including: emergence, crop yields, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The combination according to the invention can also provide an improved systemicity to the active compounds that are used. Indeed, even if some of the used fungicide compounds do not possess any or a satisfying systemicity, within the composition according to the invention these compounds can exhibit such a property.

In a similar manner, the combination according to the invention can allow an increased persistence of the fungicide efficacy of the active compounds that are employed.

Another advantage of the combination according to the invention relies in that an increased curativity is achievable.

Accordingly, the present invention provides a combination comprising:

(A) At least one compound according to formula (I)

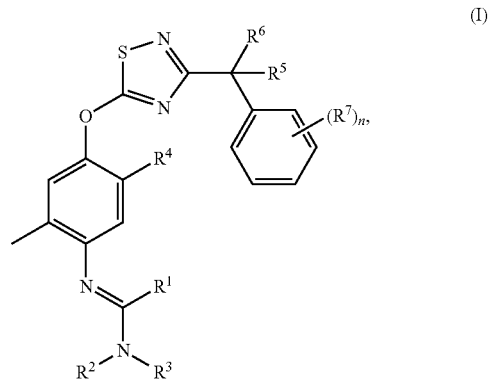

wherein $R^1$ is selected from the group consisting of hydrogen- a mercapto-(—SH) and a methyl group;

$R^2$ is selected from the group consisting of a methyl- and an ethyl group;

$R^3$ is selected from the group consisting of a methyl-, an ethyl- and an isopropyl group;

alternatively $R^2$ und $R^3$ can form, together with the N-atom, to which they are attached to, a piperidyl-, a pyrrolidyl- or a 2,6-dimethylmorpholinyl-ring;

$R^4$ is selected from the group consisting of a chlorine- or a fluorine atom, a trifluoromethyl-, a difluoromethyl- and a methyl group;

$R^5$ und $R^6$ independently from each other, is selected from the group consisting of a hydrogen atom, a methyl- and an ethyl group; or can form, together with the C-atom, to which they are attached to, a cyclopropyl ring;

R⁷ is selected from the group consisting of a chlorine atom, a tert-butyl-, a methoxy-, an ethoxy-, a trimethylsilyl- and a triethylsilyl-group, n is 1 and salts or stereoisomers thereof, and (B-I) at least one further active compound selected from the group consisting of (B-I.1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazol (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) viniconazole (77174-66-4), (1.58) 1-(4-chlorophenyl)-2-(1H-1,2,4-triazol-1-yl)cycloheptanol (129586-32-9), (1.59) methyl 1-(2,2-dimethyl-2,3-dihydro-1H-inden-1-yl)-1H-imidazole-5-carboxylate (111323-95-0), (1.60) O-{1-[(4-methoxyphenoxy)methyl]-2,2-dimethylpropyl} 1H-imidazole-1-carbothioate (111226-71-2), (1.61) N'-{5-(difluoromethyl)-2-methyl-4-[3-(trimethylsilyl)propoxy]phenyl}-N-ethyl-N-methylimidoformamide, (1.62) N-ethyl-N-methyl-N'-{2-methyl-5-(trifluoromethyl)-4-[3-(trimethylsilyl)propoxy]phenyl}imidoformamide, (1.63) voriconazole (137234-62-9), (B-I.2) inhibitors of the respiratory chain at complex I or II, for example (2.1) diflumetorim (130339-07-0), (2.2) bixafen (581809-46-03), (2.3) boscalid (188425-85-6), (2.4) carboxin (5234-68-4), (2.5) fenfuram (24691-80-3), (2.6) fluopyram (658066-35-4), (2.7) flutolanil (66332-96-5), (2.8) furametpyr (123572-88-3), (2.9) furmecyclox (60568-05-0), (2.10) isopyrazam (mixture of syn-epimeric racemate 1RS,4SR,9RS and anti-epimeric racemate 1RS,4SR,9SR) (88165-58-1), (2.11) isopyrazam (syn epimeric racemate 1RS,4SR,9RS), (2.12) isopyrazam (syn-epimeric enantiomer 1R,4S,9R), (2.13) isopyrazam (syn-epimeric enantiomer 1S,4R,9S), (2.14) isopyrazam (anti-epimeric racemate 1RS,4SR,9SR), (2.15) isopyrazam (anti-epimeric enantiomer 1R,4S,9S), (2.16) isopyrazam (anti-epimeric enantiomer 1S,4R,9R), (2.17) mepronil (55814-41-0), (2.18) oxycarboxin (5259-88-1), (2.19) penflufen (494793-67-8), (2.20) penthiopyrad (183675-82-3), (2.21) sedaxane (874967-67-6), (2.22) thifluzamide (130000-40-7), (2.23) 1-methyl-N-[2-(1,1,2,2-tetrafluoroethoxy)phenyl]-3-(trifluoromethyl)-1H-pyrazole-4-carboxamide, (2.24) 3-(difluoromethyl)-1-methyl-N-[2-(1,1,2,2-tetrafluoroethoxy)phenyl]-1H-pyrazole-4-carboxamide, (2.25) 3-(difluoromethyl)-N-[4-fluoro-2-(1,1,2,3,3,3-hexafluoropropoxy)phenyl]-1-methyl-1H-pyrazole-4-carboxamide, (2.26) 1-methyl-3-(trifluoromethyl)-N-[2'-(trifluoromethyl)biphenyl-2-yl]-1H-pyrazole-4-carboxamide, (2.27) N-(4'-chlorobiphenyl-2-yl)-3-(difluoromethyl)-1-methyl-1H-pyrazole-4-carboxamide, (2.28) N-(2',4'-dichlorobiphenyl-2-yl)-3-(difluoromethyl)-1-methyl-1H-pyrazole-4-carboxamide, (2.29) 3-(difluoromethyl)-1-methyl-N-[4'-(trifluoromethyl)biphenyl-2-yl]-1H-pyrazole-4-carboxamide, (2.30) N-(2',5'-difluorobiphenyl-2-yl)-1-methyl-3-(trifluoromethyl)-1H-pyrazole-4-carboxamide, (2.31) 3-(difluoromethyl)-1-methyl-N-[4'-(prop-1-yn-1-yl)biphenyl-2-yl]-1H-pyrazole-4-carboxamide (known from WO 2004/058723), (2.32) 5-fluoro-1,3-dimethyl-N-[4'-(prop-1-yn-1-yl)biphenyl-2-yl]-1H-pyrazole-4-carboxamide (known from WO 2004/058723), (2.33) 2-chloro-N-[4'-(prop-1-yn-1-yl)biphenyl-2-yl]pyridine-3-carboxamide (known from WO 2004/058723), (2.34) 3-(difluoromethyl)-N-[4'-(3,3-dimethylbut-1-yn-1-yl)biphenyl-2-yl]-1-methyl-1H-pyrazole-4-carboxamide (known from WO 2004/058723), (2.35) N-[4'-(3,3-dimethylbut-1-yn-1-yl)biphenyl-2-yl]-5-fluoro-1,3-dimethyl-1H-pyrazole-4-carboxamide (known from WO 2004/058723), (2.36) 3-(difluoromethyl)-N-(4'-ethynylbiphenyl-2-yl)-1-methyl-1H-pyrazole-4-carboxamide (known from WO 2004/058723), (2.37) N-(4'-ethynylbiphenyl-2-yl)-5-fluoro-1,3-dimethyl-1H-pyrazole-4-carboxamide (known from WO 2004/058723), (2.38) 2-chloro-N-(4'-ethynylbiphenyl-2-yl)pyridine-3-carboxamide (known from WO 2004/058723), (2.39) 2-chloro-N-[4'-(3,3-dimethylbut-1-yn-1-yl)biphenyl-2-yl]pyridine-3-carboxamide (known from WO 2004/058723), (2.40) 4-(difluoromethyl)-2-methyl-N-[4'-(trifluoromethyl)biphenyl-2-yl]-1,3-thiazole-5-carboxamide (known from WO 2004/058723), (2.41) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (2.42) 2-chloro-N-[4'-(3-hydroxy-3-methylbut-1-yn-1-yl)biphenyl-2-yl]pyridine-3-carboxamide (known from WO 2004/058723), (2.43) 3-(difluoromethyl)-N-[4'43-methoxy-3-methylbut-1-yn-1-yl)biphenyl-2-yl]-1-methyl-1H-pyrazole-4-carboxamide (known from WO 2004/058723), (2.44) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (2.45) 3-(difluoromethyl)-1-methyl-N-(3',4',5'-trifluorobiphenyl-2-yl)-1H-pyrazole-4-carboxamide, (2.46) 2-chloro-N-[4'-(3-methoxy-3-methylbut-1-yn-1-yl)biphenyl-2-yl]pyridine-3-carboxamide (known from WO 2004/058723) and salts or stereoisomers thereof, (B-I.3) inhibitors of the respiratory chain at complex III, for example (3.1) amisulbrom (348635-87-0), (3.2) azoxystrobin (131860-33-8), (3.3) cyazofamid (120116-88-3), (3.4) dimoxystrobin (141600-52-4), (3.5) enestroburin (238410-11-2), (3.6) famoxadone (131807-57-3), (3.7) fenamidone (161326-34-7), (3.8) fluoxastrobin (361377-29-9), (3.9) kresoxim-methyl (143390-89-0), (3.10) metominostrobin (133408-50-1), (3.11) orysastrobin (189892-69-1), (3.12) picoxystrobin (117428-22-5), (3.13) pyraclostrobin (175013-18-0), (3.14) pyrametostrobin (915410-70-7), (3.15) pyraoxystrobin (862588-11-2), (3.16) pyribencarb (799247-52-2), (3.17) trifloxystrobin (141517-21-7), (3.18) 5-methoxy-2-methyl-4-(2-{[({(1E)-1-[3-(trifluoromethyl)phenyl]ethylidene}amino)oxy]methyl}-phenyl)-2,4-dihydro-3H-1,2,4-triazol-3-one, (3.19) (2E)-2-(2-{[6-(3-chloro-2-methylphenoxy)-5-fluoropyrimidin-4-yl]oxy}phenyl)-2-(methoxyimino)-N-methylmethanamide, (3.20) 2-chloro-N-(1,1,3-trimethyl-2,3-dihydro-1H-inden-4-yl)pyridine-3-carboxamide (119899-14-8), (3.21) (2E)-2-(methoxyimino)-N-methyl-2-(2-{[({(1E)-1-[3-(trifluoromethyl)phenyl]ethylidene}amino)-oxy]methyl}phenyl)ethanamide, (3.22) N-(3-ethyl-3,5,5-trimethylcyclohexyl)-3-(formylamino)-2-hydroxybenzamide (226551-21-9), (3.23) (2E)-2-(methoxyimino)-N-methyl-2-{2-[(E)-({1-[3-(trifluoromethyl)-phenyl]ethoxy}imino)methyl]phenyl}ethanamide (326896-28-0), (3.24) (2E)-2-{2-[({[(2E,3E)-4-(2,6-dichlorophenyl)but-3-en-2-ylidene]amino}oxy)-methyl]phenyl}-2-(methoxyimino)-N-methylethanamide (known from WO 02/12172), (3.25) (2E)-2-{2-[({[(1E)-1-(3-{[(E)-1-fluoro-2-phenylethenyl]-oxy}phenyl)ethylidene]amino}oxy)methyl]phenyl}-2-(methoxyimino)-N-methylethanamide (326896-28-0), (3.26) methyl (2E)-2-{2-[({cyclopropyl-[(4-methoxyphenyl)imino]methyl}thio)methyl]phenyl}-3-methoxyacrylate (149601-03-6), (3.27) N-(3-ethyl-3,5,5-trimethylcyclohexyl)-3-(formylamino)-2-hydroxybenzamide (226551-21-9), (3.28) 2-{2-[(2,5-dimethylphenoxy)methyl]phenyl}-2-methoxy-N-methylacetamide (173662-97-0) and salts thereof, (B-I.4) Inhibitors of the mitosis and cell division, for example (4.1) benomyl (17804-35-2), (4.2) carbendazim (10605-21-7), (4.3) diethofencarb (87130-20-9), (4.4) ethaboxam (162650-77-3), (4.5) fuberidazole (3878-19-1), (4.6) pencycuron (66063-05-6), (4.7) thiabendazole (148-79-8), (4.8) thiophanate-methyl (23564-05-8), (4.9) zoxamide (156052-68-5), (4.10) 5-chloro-7-(4-methylpiperidin-1-yl)-6-(2,4,6-trifluorophenyl)[1,2,4]triazolo[1,5-a]pyrimidine (214706-53-3), (4.11) chlorfenazole (3574-96-7), (4.12) thiophanate (23564-06-9), (4.13) 3-chloro-5-(6-chloropyridin-3-yl)-6-methyl-4-(2,4,6-trifluorophenyl)pyridazine (1002756-87-7) and salts thereof, (B-I.5) Compounds capable to have a multisite action, like for example (5.1) bordeaux mixture (8011-63-0), (5.2) captafol (2425-06-1), (5.3) captan (133-06-2), (5.4) chlorothalonil (1897-45-6), (5.5) dichlofluanide (1085-98-9), (5.6) dithianon (3347-22-6), (5.7) dodine (2439-10-3), (5.8) ferbam (14484-64-1), (5.9) folpet (133-07-3), (5.10) guazatine (108173-90-6), (5.11) iminoctadine (13516-27-3), (5.12) iminoctadine triacetate (57520-17-9), (5.13) iminoctadine albesilate (169202-06-6), (5.14) copper oxide (1317-39-1), (5.15) copper oxychloride (1332-40-7), (5.16) copper hydroxide (20427-59-2), (5.17) copper sulfate (7758-98-7), (5.18) mancopper (53988-93-5), (5.19) mancozeb (2234562), (5.20) maneb (12427-38-2), (5.21) metiram (9006-42-2), (5.22) oxine-copper (10380-28-6), (5.23) propineb (12071-83-9), (5.24) sulphur and sulphur preparations including calcium polysulphide (7704-34-9), (5.25) thiram (137-26-8), (5.26) tolylfluanide (731-27-1), (5.27) zineb (12122-67-7), (5.28) ziram (137-30-4), (5.29) copper naphthenate (1338-02-9), (5.30) dodine free base, (5.31) fluorofolpet (719-96-0), (5.32) guazatine acetate, (5.33) metiram zinc (9006-42-2).(5.34) propamidine (104-32-5), (B-I.6) Compounds capable to induce a host defense, like for example (6.1) acibenzolar-S-methyl (135158-54-2), (6.2) probenazole (27605-76-1), (6.3) tiadinil (223580-51-6), (B-I.7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0), (B-I.8) Inhibitors of the ATP production, for example (8.1) fentin acetate (900-95-8), (8.2) fentin hydroxide (76-87-9), (8.3) silthiofam (175217-20-6), (8.4) fentin chloride (639-58-7), (B-I.9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) prothiocarb (19622-08-3), (9.9) validamycin A (37248-47-8), (9.10) valifenalate (283159-94-4; 283159-90-0), (9.11) N-[2-(4-{[3-(4-chlorophenyl)prop-2-yn-1-yl]oxy}-3-methoxyphenyl)ethyl]-N-2-(methylsulfonyl) valinamide (220706-93-4), (B-I.10) Inhibitors of the lipid and membrane synthesis, for example (10.1) biphenyl (92-52-4), (10.2) chlozolinate (84332-86-5), (10.3) edifenphos (17109-49-8), (10.4) etridiazole (2593-15-9), (10.5) iodocarb (55406-53-6), (10.6) iprobenfos (26087-47-8), (10.7) iprodione (36734-19-7), (10.8) isoprothiolane (50512-35-1), (10.9) procymidone (32809-16-8), (10.10) propamocarb (25606-41-1), (10.11) propamocarb hydrochloride (25606-41-1), (10.12) pyrazophos (13457-18-6), (10.13) tolclofos-methyl (57018-04-9), (10.14) vinclozolin (50471-44-8), (B-I.11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2), (B-I.12) Inhibitors of the nucleic acid synthesis, for example (12.1) benalaxyl (71626-11-4), (12.2) benalaxyl-M (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (70630-17-0), (12.11) ofurace (58810-48-3), (12.12) oxadixyl (77732-09-3), (12.13) oxolinic acid (14698-29-4), (B-I.13) Inhibitors of the signal transduction, for example (13.1) fenpiclonil (74738-17-3), (13.2) fludioxonil (131341-86-1), (13.3) quinoxyfen (124495-18-7), (B-I.14) Compounds capable to act as an uncoupler, like for example (14.1) dinocap (131-72-6), (14.2) fluazinam (79622-59-6), (14.3) meptyldinocap (131-72-6), (14.4) binapacryl (485-31-4), (B-I.15) Further compounds like for example (15.1) ametoctradin (865318-97-4), (15.2) benthiazole (21564-17-0), (15.3) bethoxazin (163269-30-5), (15.4) carvone (99-49-0), (15.5) chinomethionat (2439-01-2), (15.6) cyflufenamid (180409-60-3), (15.7) cymoxanil (57966-95-7), (15.8) dazomet (533-74-4), (15.9) debacarb (62732-91-6), (15.10) dichlorophen (97-23-4), (15.11) diclomezine (62865-36-5), (15.12) dicloran (99-30-9), (15.13) difenzoquat (43222-48-6), (15.14) diphenylamine (122-39-4), (15.15) ferimzone (89269-64-7), (15.16) flumetover (154025-04-4), (15.17) fluopicolide (239110-15-7), (15.18) fluoroimide (41205-21-4), (15.19) flusulfamide (106917-52-6), (15.20) fosetyl-aluminium (39148-24-8), (15.21) hexachlorobenzene (118-74-1), (15.22) isotianil (224049-04-1), (15.23) methasulfocarb (66952-49-6), (15.24) methyl isothiocyanate (556-61-6), (15.25) metrafenone (220899-03-6), (15.26) nitrothal-isopropyl (10552-74-6), (15.27) octhilinone (26530-20-1), (15.28) oxyfenthiin (34407-87-9), (15.29) propamocarb-fosetylate, (15.30) proquinazid (189278-12-4), (15.31) pyrrolnitrine (1018-71-9), (15.32) quintozene (82-68-8), (15.33) tecloftalam (76280-91-6), (15.34) tecnazene (117-18-0), (15.35) triazoxide (72459-58-6), (15.36) trichlamide (70193-21-4), (15.37) zarilamid (84527-51-5), (15.38) quinolin-8-ol sulfate (2:1) (salt) (8-hydroxyquinoline sulfat) (134-31-6), (15.39) 2,3,5,6-tetrachloro-4-(methylsulfonyl)pyridine (13108-52-6), (15.40) 3,4,5-trichloropyridine-2,6-dicarbonitrile (17824-85-0), (15.41) 3-[5-(4-chlorophenyl)-2,3-dimethylisoxazolidin-3-yl]pyridine, (15.43) 2-butoxy-6-iodo-3-propyl-4H-chromen-4-one, (15.44) N-[1-(5-bromo-3-chloropyridin-2-yl)ethyl]-2,4-dichloropyridine-3-carboxamide, (15.45) N-[(5-bromo-3-chloropyridin-2-yl)methyl]-2,4-dichloropyridine-3-carboxamide, (15.46) N-[1-(5-bromo-3-chloropyridin-2-yl)ethyl]-2-fluoro-4-iodopyridine-3-carboxamide, (15.47) N-(4-chlorobenzyl)-3-[3-methoxy-4-(prop-2-yn-1-yloxy)phenyl]propanamide, (15.48) N-[(4-chlorophenyl)(cyano)methyl]-3-[3-methoxy-4-(prop-2-yn-1-yloxy)phenyl]propanamide, (15.49) S-prop-2-en-1-yl 5-amino-2-(1-methylethyl)-4-(2-methylphenyl)-3-oxo-2,3-dihydro-1H-pyrazole-1-carbothioate, (15.50) 2,3-dibutyl-6-chlorothieno[2,3-d]pyrimidin-4(3H)-one (221451-58-7), (15.51) ethyl (2Z)-3-amino-2-cyano-3-phenylprop-2-enoate, (15.52) 5-amino-1,3,4-thiadiazole-2-thiol, (15.53) 1-[(4-methoxy-phenoxy)methyl]-2,2-dimethylpropyl 1H-imidazole-1-carboxylate (111227-17-9), (15.54) 3-chloro-5-(4-chlorophenyl)-4-(2,6-difluorophenyl)-6-methylpyridazine, (15.55) 4-(4-chlorophenyl)-5-(2,6-difluorophenyl)-3,6-dimethylpyridazine, (15.56) tebufloquin (376645-78-2), (15.57) flutianil (304900-25-2), (15.58) (5-bromo-2-methoxy-4-methylpyridin-3-yl)(2,3,4-trimethoxy-6-methylphenyl)methanone (known from EP-A 1 559 320), (15.59) tolnifanide (304911-98-6), (15.60) N-{(Z)-[(cyclopropyl-methoxy)imino][6-(difluoromethoxy)-2,3-difluorophenyl]methyl}-2-phenyl-acetamide (221201-92-9), (15.61) N-{(E)-[(cyclopropylmethoxy)imino][6-(difluoromethoxy)-2,3-difluorophenyl]methyl}-2-phenylacetamide, (15.62) phosphorous acid and its salts (13598-36-2), (15.63) 5-chloro-N'-phenyl-N'-prop-2-yn-1-ylthiophene-2-sulfonohydrazide (134-31-6), (15.64) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.65) N-methyl-2-(1-{[5-methyl-3-(trifluoromethyl)-1H-pyrazol-1-yl]acetyl}-piperidin-4-yl)-N-(1,2,3,4-tetrahydronaphthalen-1-yl)-1,3-thiazole-4-carboxamide, (15.66) pentyl {6-[({[(1-methyl-1H-tetrazol-5-yl)(phenyl)methylidene]amino}oxy)methyl]pyridin-2-yl}carbamate, (15.67) capsimycin (70694-08-5), (15.68) chloroneb (2675-77-6), (15.69) cufraneb (11096-18-7), (15.70) cyprosulfamide (221667-31-8), (15.71) difenzoquat methylsulphate (43222-48-6), (15.72) ecomate, (15.73) fosetyl-calcium, (15.74) fosetyl-sodium (39148-16-8), (15.75) irumamycin (81604-73-1), (15.76) mildiomycin (67527-71-3), (15.77) natamycin (7681-93-8), (15.78) nickel dimethyldithiocarbamate (15521-65-0), (15.79) oxamocarb (917242-12-7), (15.80) pentachlorophenol and salts (87-86-5), (15.81) phenazine-1-carboxylic acid, (15.82) phenothrin, (15.83) propanosine-sodium (88498-02-6), (15.84) quinolin-8-ol (134-31-6), (15.85) 2- phenylphenol and salts (90-43-7), (15.86) 5-methyl-6-octyl-3,7-dihydro[1,2,4]triazolo[1,5-a]pyrimidin-7-amine, (15.87) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.88) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone and salts thereof, or (B-II) at least one further insecticidally active compound, selected from the group consisting of (B-II.1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, and xylylcarb; or organophosphates, e.g. acephate, azamethiphos, azinphos (-methyl, -ethyl), cadusafos, chlorethoxyfos, chlorfenvinphos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon, and vamidothion, (B-II.2) GABA-gated chloride channel antagonists, for example organochlorines, e.g. chlordane, endosulfan (alpha-); or fiproles (phenylpyrazoles), e.g. ethiprole, fipronil, pyrafluprole, and pyriprole, (B-II.3) Sodium channel modulators/voltage-dependent sodium channel blockers, for example pyrethroids, e.g. acrinathrin, allethrin (d-cis-trans, d-trans), bifenthrin, bioallethrin, bioallethrin S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers), esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer), prallethrin, profluthrin, pyrethrin (pyrethrum), resmethrin, RU 15525, silafluofen, tefluthrin, tetramethrin [(1R)-isomers)], tralomethrin, transfluthrin and ZXI 8901; or DDT; or methoxychlor, (B-II.4) Nicotinergic acetylcholine receptor agonists, for example chloronicotinyls, e.g. acetamiprid, clothianidin, dinotefuran, imidacloprid, nitenpyram, thiacloprid, thiamethoxam; or nicotine, (B-II.5) Allosteric acetylcholine receptor modulators (agonists), for example spinosyns, e.g. spinetoram and spinosad, (B-II.6) Chloride channel activators, for example avermectins/milbemycins, e.g. abamectin, emamectin benzoate, lepimectin, and milbemectin, (B-II.7) Juvenile hormone mimics, e.g. hydroprene, kinoprene, methoprene; or fenoxycarb; pyriproxyfen, (B-II.8) Miscellaneous non-specific (multi-site) inhibitors, for example_gassing agents, e.g. methyl bromide and other alkyl halides; or chloropicrin; sulfuryl fluoride; borax; tartar emetic, (B-II.9) Selective homopteran feeding blockers, e.g. pymetrozine or flonicamid, (B-II.10) Mite growth inhibitors, e.g. clofentezine, diflovidazin, hexythiazox, etoxazole, (B-II.11) Microbial disruptors of insect midgut membranes, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1, (B-II.12) Inhibitors of mitochondrial ATP synthase, for example diafenthiuron; or organotin miticides, e.g. azocyclotin, cyhexatin, and fenbutatin oxide; or propargite; tetradifon, (B-II.13) Uncouplers of oxidative phosphorylation via disruption of the proton gradient, for example chlorfenapyr, and DNOC, (B-II.14) Nicotinic acetylcholine receptor channel blockers, for example bensultap, cartap hydrochloride, thiocyclam, and thiosultap-sodium, (B-II.15) Inhibitors of chitin biosynthesis, type 0, for example benzoylureas, e.g. bistrifluoron, chlorfluazuron, diflubenzuron, flucycloxuron, flufenoxuron, hexaflumuron, lufenuron, novaluron, noviflumuron, penfluoron, teflubenzuron, and triflumuron, (B-II.16) Inhibitors of chitin biosynthesis, type 1, for example buprofezin, (B-II.17) Molting disruptors, for example cyromazine, (B-II.18) Ecdysone receptor agonists/disruptors, for example diarylhydrazines, e.g. chromafenozide, halofenozide, methoxyfenozide, and tebufenozide, (B-II.19) Octopamine receptor agonists, for example amitraz, (B-II.20) Mitochondrial complex III electron transport inhibitors, for example hydramethylnon; acequinocyl or fluacrypyrim, (B-II.21) Mitochondrial complex I electron transport inhibitors, for example METI acaricides, e.g. fenazaquin, fenpyroximate, pyrimidifen, pyridaben, tebufenpyrad, tolfenpyrad or rotenone (Derris), (B-II.22) Voltage-dependent sodium channel blockers, e.g. indoxacarb; metaflumizone, (B-II.23) Inhibitors of acetyl CoA carboxylase, for example tetronic acid derivatives, e.g. spirodiclofen and spiromesifen; or tetramic acid derivatives, e.g. spirotetramat, (B-II.24) Mitochondrial complex IV electron inhibitors, for example phosphines, e.g. aluminium phosphide, calcium phosphide, phosphine, and zinc phosphide or cyanide, (B-II.25) Mitochondrial complex II electron transport inhibitors, for example cyenopyrafen, (B-II.28) Ryanodine receptor modulators, for example diamides, e.g. chlorantraniliprole (Rynaxypyr), Cyantraniliprole (Cyazypyr), and flubendiamide, (B-II.29) Further active ingredients with unknown or uncertain mode of action, for example azadirachtin, amidoflumet, benzoximate, bifenazate, chinomethionat, cryolite, cyflumetofen, dicofol, flufenerim, pyridalyl, and pyrifluquinazon; or one of the following known active compounds 4-{[(6-bromopyrid-3-yl)methyl] (2-fluorethyl)amino}furan-2(5H)-on (known from WO 2007/115644), 4-{[(6-fluoropyrid-3-yl)methyl](2,2-difluorethyl)amino}-furan-2(5H)-on (known from WO 2007/115644), 4-{[(2-chlor-1,3-thiazol-5-yl)methyl] (2-fluorethyl)amino}furan-2(5H)-on (known from WO 2007/115644), 4-{[(6-chloropyrid-3-yl)methyl](2-fluorethyl)amino}furan-2(5H)-on (known from WO 2007/115644), 4-{[(6-chloropyrid-3-yl)methyl](2,2-difluorethyl)amino}furan-2(5H)-on known from WO 2007/115644), 4-{[(6-chlor-5-fluoropyrid-3-yl)methyl] (methyl)amino}furan-2(5H)-on (known from WO 2007/115643), 4-{[(5,6-dichloropyrid-3-yl)methyl](2-fluorethyl)amino}furan-2(5H)-on (known from WO 2007/115646), 4-{[(6-chlor-5-fluoropyrid-3-yl)methyl] (cyclopropyl)amino}-furan-2(5H)-on (known from WO 2007/115643), 4-{[(6-chloropyrid-3-yl)methyl](cyclopropyl)amino}furan-2(5H)-on (known from EP-A-0 539 588), 4-{[(6-chloropyrid-3-yl)methyl] (methyl) amino}furan-2(5H)-on (known from EP-A-0 539 588), [(6-chloropyridin-3-yl)methyl] (methyl)oxido-λ$^4$-sulfanylidencyanamid (known from WO 2007/149134), [1-(6-chloropyridin-3-yl)ethyl](methyl)oxido-λ$^4$-sulfanylidencyanamid (known from WO 2007/149134) and its diastereomers (A) and (B)

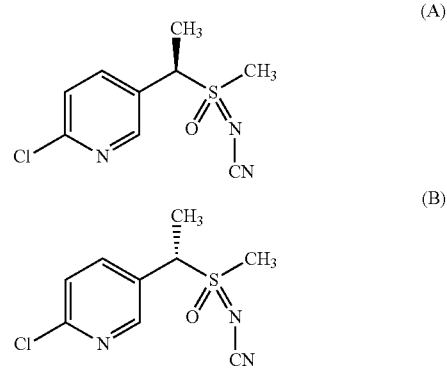

(also known from WO 2007/149134), [(6-trifluoromethylpyridin-3-yl)methyl](methyl)-oxido-λ$^4$-sulfanylidencyanamid (known from WO 2007/095229), or sulfoxaflor (also known from WO 2007/149134), 11-(4-chloro-2,6-dimethylphenyl)-

12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), and 1-{2,4-dimethyl-5-[(2,2,2-trifluoroethyl)-sulfinyl]phenyl}-3-(trifluoromethyl)-1H-1,2,4-triazole (known from WO 1999/55668); fluensulfone (5-chloro-2-[(3,4,4-trifluorobut-3-en-1-yl)sulfonyl]-1,3-thiazole), 1-[2-fluoro-4-methyl-5-[(2,2,2-trifluoroethyl)sulfinyl]phenyl]-3-(trifluoromethyl)-1H-1,2,4-Triazol-5-amine (bekannt aus WO 2006/043635), [(3S,4aR,12R,12aS,12bS)-3-[(Cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methylcyclopropancarboxylat (bekannt aus WO 2006/129714), 2-Cyan-3-(difluoromethoxy)-N,N-dimethylbenzolsulfonamid (bekannt aus WO2006/056433), 2-Cyan-3-(difluoromethoxy)-N-methylbenzolsulfonamid (bekannt aus WO2006/100288), 2-Cyan-3-(difluoromethoxy)-N-ethylbenzolsulfonamid (bekannt aus WO2005/035486), 4-(Difluoromethoxy)-N-ethyl-N-methyl-1,2-benzothiazol-3-amin-1,1-dioxid (bekannt aus WO2007/057407), N-[1-(2,3-Dimethylphenyl)-2-(3,5-dimethylphenyl)ethyl]-4,5-dihydro-1,3-thiazol-2-amin (bekannt aus WO2008/104503) furthermore products based on *Bacillus firmus* (I-1582, BioNeem, Votivo), or (B-III) at least one compound having plant growth regulating activity, selected from the group consisting of (B-III.1) antiauxines for example clofibrin [2-(4-chlorophenoxy)-2-methylpropionic acid] and 2,3,5-tri-iodobenzoic acid, (B-III.2) auxines, e.g. 4-CPA (4-chlorophenoxyacetic acid), 2,4-D (2,4-dichlorophenoxyacetic acid), 2,4-DB [4-(2,4-dichlorophenoxy)butyric acid], 2,4-DEP {tris [2-(2,4-dichlorophenoxy)ethyl]phosphite}, dichlorprop, fenoprop, IAA (β-indoleacetic acid), IBA (4-indol-3-ylbutyric acid), naphthaleneacetamide, α-naphthaleneacetic acid, 1-naphthol, naphthoxyacetic acid, potassium naphthenate, sodium naphthenate, 2,4,5-T [(2,4,5-trichlorophenoxy)acetic acid], (B-III.3) cytokinines, e.g. 2iP [N-(3-methylbut-2-enyl)-1H-purine-6-amine], benzyladenine, kinetin, zeatin, (B-III.4) defoliating agents, for instance, calcium cyanamide, dimethipin, endothal, ethephon, merphos, metoxuron, pentachlorophenol, thidiazuron, tribufos, (B-III.5) ethylene inhibitors, e.g. aviglycine, aviglycine-hydrochloride, 1-methylcyclopropen, (B-III.6) ethylene generators, e.g. ACC (1-aminocyclopropancarboxylic acid), etacelasil, ethephon, glyoxime, (B-III.7) gibberellines, such as gibberellines A1, A4, A7, gibberellinic acid (=gibberellin A3), (B-III.8) further PGRs, such as abscisinic acid, ancymidol, butralin, carbaryl, chlorphonium or its chloride, chlorpropham, dikegulac, dikegulac-sodium, flumetralin, fluoridamide, fosamine, glyphosine, isopyrimol, jasmonic acid, maleic acid hydrazide or its potassium salt, mepiquat or its chloride, piproctanyl or its bromide, prohydrojasmon, propham, 2,3,5-tri-iodobenzoic acid, 2,6-diisopropylnaphthaline, cloprop, 1-naphthylacetic acid ethylester, isoprothiolane, MCPB-ethyl [4-(4-Cchloro-o-tolyloxy)butyric acid ethylester], N-acetylthiazolidine-4-carboxylic acid, n-decanol, pelargonic acid, N-phenylphthaliminic acid, tecnazene, triacontanol, 2,3-dihydro-5,6-diphenyl-1,4-oxathiin, 2-cyano-3-(2,4-dichlorophenyl)acrylic acid, 2-hydrazinoethanol, alorac, amidochlor, BTS 44584 [dimethyl(4-piperidinocarbonyloxy-2,5-xylyl)sulfonium-toluen-4-sulfonat], chloramben, chlorfluren, chlorfluren-methyl, dicamba-methyl, dichlorfurenol, dichlorfurenol-methyl, dimexano, etacelasil, hexafluoraceton-trihydrat, N-(2-ethyl-2H-pyrazol-3-yl)-N'-phenylurea, N-m-tolylphthalaminic acid, N-Pyrrolidinosuccinaminic acid, 3-tert-Butylphenoxyacetic acid propylester, pydanon, sodium (Z)-3-chloroacrylate, (B-III.9) morphactines, such as chlorfluren, chloroflurenol, chloroflurenol-methyl, dichlorflurenol, fluorenol, (B-III.10) plant growth retarder/modifier, such as chlormequat, chlormequat-chlorid, daminozide, flurprimidol, mefluidide, mefluidide-diolamin, paclobutrazol, cyproconazole, tetcyclacis, uniconazole, uniconazole-P, (B-III.11) plant growth stimulators, such as brassinolides, forchlorfenuron, hymexazol, 2-amino-6-oxypurine derivatives, indolinon derivatives, 3,4-disubstituted maleimide derivatives and azepinon derivatives, (B-III.12) non-classified PGRs, such as benzofluor, buminafos, carvone, ciobutide, clofencet, clofence-potassium, cloxyfonac, cloxyfonac-Natrium, cyclanilide, cycloheximide, epocholeone, ethychlozate, ethylene, fenridazon, heptopargil, holosulf, inabenfide, karetazan, leadarsenate, methasulfocarb, prohexadione, prohexadione-Calcium, pydanon, sintofen, triapenthenol, trinexapac and trinexapac-ethyl.

Preference is given to combinations comprising compounds of the formula (I), wherein the amidine derivatives are represented by the following formula (Ia):

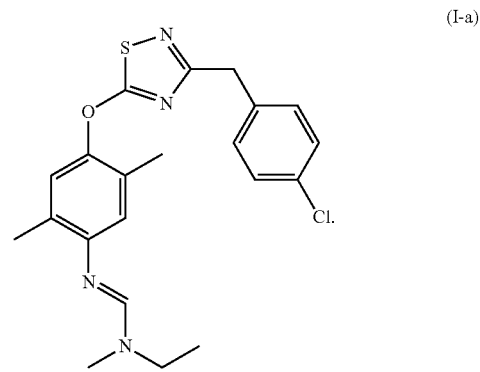 [SMILES: CCN(C)/C=N/c1cc(C)c(Oc2nc(Cc3ccc(Cl)cc3)ns2)cc1C]

(I-a)

Preference is further given to combinations comprising a compound (B-I) selected from the list consisting of Cyproconazole, Epoxiconazole, Flusilazole, Fluquinconazole Ipconazole, Propiconazole, Prothioconazole, Metconazole, Tebuconazole, Triadimenol, Azoxystrobin, Fluoxastrobin, Kresoxim-methyl, Picoxystrobin, Pyraclostrobin, Trifloxystrobin, Boscalid, Chlorothalonil, Cyprodinil, Fludioxonil, Fluopyram, Thiophanat-methyl, Penflufen, Isopyrazam, Sedaxane, Myclobutonil, Prochloraz, Spiroxamine, N-(3',4'-dichloro-5-fluoro[1,1'-biphenyl]-2-yl)-3-(difluoromethyl)-1-methyl-1H-pyrazole-4-carboxamide, Ametoctradin, 5-Chlor-6-(2,4,6-trifluorophenyl)-7-(4-methylpiperidin-1-yl) [1,2,4]triazolo[1,5-a]pyrimidin, 1-methyl-N-{2-[1'-methyl-1,1'-bi(cyclopropyl)-2-yl]phenyl}-3-(trifluoromethyl)-1H-pyrazole-4-carboxamide, 1-methyl-N-{2-[1'-methyl-1,1'-bi(cyclopropyl)-2-yl]phenyl}-3-(difluoromethyl)-1H-pyrazole-4-carb oxamide, N-{2-[1,1'-bi(cyclopropyl)-2-yl]phenyl}-1-methyl-3-(difluoromethyl)-1H-pyrazole-4-carboxamide.

Preference is further given to combinations comprising an insecticidally active compound (B-II) selected from the list consisting of Acephate, Acequinocyl, Acrinathrin, Aldicarb, Amitraz, Anthraquinone, Azinphos-Methyl, Azocyclotin, Bendiocarb, Benfuracarb, Bifenthrin, Buprofezin, Carbaryl, Carbofuran, Carbosulfan, Cartap, Chlorfluazuron, Chlorpyrifos, Chlorpyrifos-M, Clofentezine, Clothianidin, Cyfluthrin, Cyhexatin, Cypermethrin, Cyromazine, Deltamethrin, Diazinon, Dichloropropene, Dichlorvos, Dimethoate, Disulfoton, Ethion, Ethiprole, Ethoprophos, Etofenprox, Fenamiphos, Fenitrothion, Fenobucarb, Fenpyroximate, Fenthion, Fipronil, Flubendiamide, Formetanate, Heptenophos, Hexythiazox, Imidacloprid, Metaldehyde, Methamidophos, Methiocarb, Methomyl, Methoxyfenozide, Milbemectin, M-Isothiocyanate, Permethrin, Phenthoate, Phosalone, Phoxim, Polyeder-Nuclear-Vir, Profenofos, Propargite, Prothiofos, Pyrethroids, Pyriproxifen, Quinalphos, Quinomethionate, Resmethrin, Silafluofen, Sodium-Tetrathiocarbonate, Spinosad, Spirodiclofen, Spiromesifen, Spirotetramat, Tebupirimphos, Tefluthrin, Thiacloprid, Thiamethoxam, Thiodicarb, Triazophos, Trichlorfon, Triflumuron.

Preference is further given to combinations comprising a compound (B-III) selected from the list consisting of chlormequat, chlormequat-chloride, cyclanilide, dimethipin, ethephon, flumetralin, flurprimidol, inabenfide, mepiquat, mepiquat-chlorid, 1-methylcyclopropen, paclobutrazol, prohexadione-calcium, prohydrojasmon, tribufos, thidiazuron, trinexapac, trinexapac-ethyl and uniconazole.

Particular preference is given to combinations comprising an active compound (B-I) selected from the list consisting of Prothioconazole, Tebuconazole, Metconazole, Epoxiconazole, Fluquinconazole, Prochloraz, Carbendazim, Thiophanat-methyl, Myclobutanil, Dimoxystrobin, Fluopyram, Fludioxonil.

Particular preference is given to combinations comprising an active compound (B-III) selected from the list consisting of trinexapac-ethyl, chlormequat-chloride and paclobutrazol.

For most of the compounds of group (B-I) to (B-III) it is referred to The Pesticide Manual, 15$^{th}$ edition, 2009. The compounds (B) are listed by common names followed by the corresponding CAS-numbers in parenthesis. If no common name was available at the priority date of the application compounds (B) are listed by IUPAC-names followed by the corresponding CAS-numbers in parenthesis.

Particularly preferred combinations and or compositions comprise the amidine of formula (Ia) and at least one compound of group (B-I), which is selected from the group consisting of (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazol (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) viniconazole (77174-66-4), (1.58) 1-(4-chlorophenyl)-2-(1H-1,2,4-triazol-1-yl)cycloheptanol (129586-32-9), (1.59) methyl 1-(2,2-dimethyl-2,3-dihydro-1H-inden-1-yl)-1H-imidazole-5-carboxylate (111323-95-0), (1.60) O-{1-[(4-methoxyphenoxy)methyl]-2,2-dimethylpropyl}1H-imidazole-1-carbothioate (111226-71-2), (1.61) N'-{5-(difluoromethyl)-2-methyl-4-[3-(trimethyl silyl)-propoxy]phenyl}-N-ethyl-N-methylimidoformamide, (1.62) N-ethyl-N-methyl-N'-{2-methyl-5-(trifluoromethyl)-4-[3-(trimethylsilyl)propoxy]phenyl}imidoformamide, (1.63) voriconazole (137234-62-9); (2.1) diflumetorim (130339-07-0), (2.2) bixafen (581809-46-03), (2.3) boscalid (188425-85-6), (2.4) carboxin (5234-68-4), (2.5) fenfuram (24691-80-3), (2.6) fluopyram (658066-35-4), (2.7) flutolanil (66332-96-5), (2.8) furametpyr (123572-88-3), (2.9) furmecyclox (60568-05-0), (2.10) isopyrazam (mixture of syn-epimeric racemate 1RS,4SR,9RS and anti-epimeric racemate 1RS,4SR,9SR) (88165-58-1), (2.11) isopyrazam (syn epimeric racemate 1RS,4SR,9RS), (2.12) isopyrazam (syn-epimeric enantiomer 1R,4S,9R), (2.13) isopyrazam (syn-epimeric enantiomer 1S,4R,9S), (2.14) isopyrazam (anti-epimeric racemate 1RS,4SR,9SR), (2.15) isopyrazam (anti-epimeric enantiomer 1R,4S,9S), (2.16) isopyrazam (anti-epimeric enantiomer 1S,4R,9R), (2.17) mepronil (55814-41-0), (2.18) oxycarboxin (5259-88-1), (2.19) penflufen (494793-67-8), (2.20) penthiopyrad (183675-82-3), (2.21) sedaxane (874967-67-6), (2.22) thifluzamide (130000-40-7), (2.23) 1-methyl-N-[2-(1,1,2,2-tetrafluoroethoxy)phenyl]-3-(trifluoromethyl)-1H-pyrazole-4-carboxamide, (2.24) 3-(difluoromethyl)-1-methyl-N-[2-(1,1,2,2-tetrafluoroethoxy) phenyl]-1H-pyrazole-4-carboxamide, (2.25) 3-(difluoromethyl)-N-[4-fluoro-2-(1,1,2,3,3,3-hexafluoropropoxy)phenyl]-1-methyl-1H-pyrazole-4-carboxamide, (2.26) 1-methyl-3-(trifluoromethyl)-N-[2'-(trifluoromethyl) biphenyl-2-yl]-1H-pyrazole-4-carboxamide, (2.27) N-(4'-chlorobiphenyl-2-yl)-3-(difluoromethyl)-1-methyl-1H-pyrazole-4-carboxamide, (2.28) N-(2',4'-dichlorobiphenyl-2-yl)-3-(difluoromethyl)-1-methyl-1H-pyrazole-4-carboxamide, (2.29) 3-(difluoromethyl)-1-methyl-N-[4'-(trifluoromethyl)biphenyl-2-yl]-1H-pyrazole-4-carboxamide, (2.30) N-(2',5'-difluorobiphenyl-2-yl)-1-methyl-3-(trifluoromethyl)-1H-pyrazole-4-carboxamide, (2.31) 3-(difluoromethyl)-1-methyl-N-[4'-(prop-1-yn-1-yl) biphenyl-2-yl]-1H-pyrazole-4-carboxamide (known from WO 2004/058723), (2.32) 5-fluoro-1,3-dimethyl-N-[4'-(prop-1-yn-1-yl)biphenyl-2-yl]-1H-pyrazole-4-carboxamide (known from WO 2004/058723), (2.33) 2-chloro-N-[4'-(prop-1-yn-1-yl)biphenyl-2-yl]pyridine-3-carboxamide (known from WO 2004/058723), (2.34) 3-(difluoromethyl)-N-[4'-(3,3-dimethylbut-1-yn-1-yl)biphenyl-2-yl]-1-methyl-1H-pyrazole-4-carboxamide (known from WO 2004/058723), (2.35) N-[4'-(3,3-dimethylbut-1-yn-1-yl)biphenyl-2-yl]-5-fluoro-1,3-dimethyl-1H-pyrazole-4-carboxamide (known from WO 2004/058723), (2.36) 3-(difluoromethyl)-N-(4'-ethynylbiphenyl-2-yl)-1-methyl-1H-pyrazole-4-carboxamide (known from WO 2004/058723), (2.37) N-(4'-ethynylbiphenyl-2-yl)-5-fluoro-1,3-dimethyl-1H-pyrazole-4-carboxamide (known from WO 2004/058723), (2.38) 2-chloro-N-(4'-ethynylbiphenyl-2-yl)pyridine-3-carboxamide (known from WO 2004/058723), (2.39) 2-chloro-N-[4'-(3,3-dimethylbut-1-yn-1-yl)biphenyl-2-yl]pyridine-3-carboxamide (known from WO 2004/058723), (2.40) 4-(difluoromethyl)-2-methyl-N-[4'-(trifluoromethyl)biphenyl-2-yl]-1,3-thiazole-5-carboxamide (known from WO 2004/058723), (2.41) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (2.42) 2-chloro-N-[4'-(3-hydroxy-3-methylbut-1-yn-1-yl)biphenyl-2-yl]pyridine-3-carboxamide (known from WO 2004/058723), (2.43) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (2.44) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (2.45) 3-(difluoromethyl)-1-methyl-N-(3',4',5'-trifluorobiphenyl-2-yl)-1H-pyrazole-4-carboxamide, (2.46) 2-chloro-N-[4'-(3-methoxy-3-methylbut-1-yn-1-yl)biphenyl-2-yl]pyridine-3-carboxamide (known from WO 2004/058723), (3.1) amisulbrom (348635-87-0), (3.2) azoxystrobin (131860-33-8), (3.3) cyazofamid (120116-88-3), (3.4) dimoxystrobin (141600-52-4), (3.5) enestroburin (238410-11-2), (3.6) famoxadone (131807-57-3), (3.7) fenamidone (161326-34-7), (3.8) fluoxastrobin (361377-29-9), (3.9) kresoxim-methyl (143390-89-0), (3.10) metominostrobin (133408-50-1), (3.11) orysastrobin (189892-69-1), (3.12) picoxystrobin (117428-22-5), (3.13) pyraclostrobin (175013-18-0), (3.14) pyrametostrobin (915410-70-7), (3.15) pyraoxystrobin (862588-11-2), (3.16) pyribencarb (799247-52-2), (3.17) trifloxystrobin (141517-21-7), (3.18) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.19) (2E)-2-(2-{[6-(3-chloro-2-methylphenoxy)-5-fluoropyrimidin-4-yl]oxy}phenyl)-2-(methoxyimino)-N-methylethanamide, (3.20) 2-chloro-N-(1,1,3-trimethyl-2,3-dihydro-1H-inden-4-yl)pyridine-3-carboxamide (119899-14-8), (3.21) (2E)-2-(methoxyimino)-N-methyl-2-(2-{[({(1E)-1-[3-(trifluoromethyl)-phenyl]ethylidene}amino)oxy]methyl}phenyl)ethanamide, (3.22) N-(3-ethyl-3,5,5-trimethylcyclohexyl)-3-(formylamino)-2-hydroxybenzamide (226551-21-9), (3.23) (2E)-2-(methoxyimino)-N-methyl-2-{2-[(E)-({1-[3-(trifluoromethyl)phenyl]ethoxy}imino)methyl]-phenyl}ethanamide (326896-28-0), (3.24) (2E)-2-{2-[({[(2E,3E)-4-(2,6-dichlorophenyl)but-3-en-2-ylidene]amino}oxy)methyl]phenyl}-2-(methoxyimino)-N-methylethanamide (known from WO 02/12172), (3.25) (2E)-2-{2-[({[(1E)-1-(3-{[(E)-1-fluoro-2-phenylethenyl]oxy}phenyl)-ethylidene]amino}oxy)methyl]phenyl}-2-(methoxyimino)-N-methylethanamide (326896-28-0), (3.26) methyl (2E)-2-{2-[({cyclopropyl[(4-methoxyphenyl)imino]methyl}thio)methyl]phenyl}-3-methoxyacrylate (149601-03-6), (3.27) N-(3-ethyl-3,5,5-trimethylcyclohexyl)-3-(formylamino)-2-hydroxybenzamide (226551-21-9), (3.28) 2-{2-[(2,5-dimethylphenoxy)methyl]phenyl}-2-methoxy-N-methylacetamide (173662-97-0), (4.1) benomyl (17804-35-2), (4.2) carbendazim (10605-21-7), (4.3) diethofencarb (87130-20-9), (4.4) ethaboxam (162650-77-3), (4.5) fuberidazole (3878-19-1), (4.6) pencycuron (66063-05-6), (4.7) thiabendazole (148-79-8), (4.8) thiophanate-methyl (23564-05-8), (4.9) zoxamide (156052-68-5), (4.10) 5-chloro-7-(4-methylpiperidin-1-yl)-6-(2,4,6-trifluorophenyl)[1,2,4]triazolo[1,5-a]pyrimidine (214706-53-3), (4.11) chlorfenazole (3574-96-7), (4.12) thiophanate (23564-06-9); (4.13) 3-chloro-5-(6-chloropyridin-3-yl)-6-methyl-4-(2,4,6-trifluorophenyl)pyridazine (1002756-87-7), (5.1) bordeaux mixture (8011-63-0), (5.2) captafol (2425-06-1), (5.3) captan (133-06-2), (5.4) chlorothalonil (1897-45-6), (5.5) dichlofluanide (1085-98-9), (5.6) dithianon (3347-22-6), (5.7) dodine (2439-10-3), (5.8) ferbam (14484-64-1), (5.9) folpet (133-07-3), (5.10) guazatine (108173-90-6), (5.11) iminoctadine (13516-27-3), (5.12) iminoctadine triacetate (57520-17-9), (5.13) iminoctadine albesilate (169202-06-6), (5.14) copper oxide (1317-39-1), (5.15) copper oxychloride (1332-40-7), (5.16) copper hydroxide (20427-59-2), (5.17) copper sulfate (7758-98-7), (5.18) mancopper (53988-93-5), (5.19) mancozeb (2234562), (5.20) maneb (12427-38-2), (5.21) metiram (9006-42-2), (5.22) oxine-copper (10380-28-6), (5.23) propineb (12071-83-9), (5.24) sulphur and sulphur preparations including calcium polysulphide (7704-34-9), (5.25) thiram (137-26-8), (5.26) tolylfluanide (731-27-1), (5.27) zineb (12122-67-7), (5.28) ziram (137-30-4), (5.29) copper naphthenate (1338-02-9), (5.30) dodine free base, (5.31) fluorofolpet (719-96-0), (5.32) guazatine acetate, (5.33) metiram zinc (9006-42-2). (5.34) propamidine (104-32-5); (6.1) acibenzolar-S-methyl (135158-54-2), (6.2) probenazole (27605-76-1), (6.3) tiadinil (223580-51-6); (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0); (8.1) fentin acetate (900-95-8), (8.2) fentin hydroxide (76-87-9), (8.3) silthiofam (175217-20-6), (8.4) fentin chloride (639-58-7); (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) prothiocarb (19622-08-3), (9.9) validamycin A (37248-47-8), (9.10) valifenalate (283159-94-4; 283159-90-0), (9.11) N-[2-(4-{[3-(4-chlorophenyl)prop-2-yn-1-yl]oxy}-3-methoxyphenyl)ethyl]-N2-(methylsulfonyl)valinamide (220706-93-4); (10.1) biphenyl (92-52-4), (10.2) chlozolinate (84332-86-5), (10.3) edifenphos (17109-49-8), (10.4) etridiazole (2593-15-9), (10.5) iodocarb (55406-53-6), (10.6) iprobenfos (26087-47-8), (10.7) iprodione (36734-19-7), (10.8) isoprothiolane (50512-35-1), (10.9) procymidone (32809-16-8), (10.10) propamocarb (25606-41-1), (10.11) propamocarb hydrochloride (25606-41-1), (10.12) pyrazophos (13457-18-6), (10.13) tolclofos-methyl (57018-04-9), (10.14) vinclozolin (50471-44-8); (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2); (12.1) benalaxyl (71626-11-4), (12.2) benalaxyl-M (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (70630-17-0), (12.11) ofurace (58810-48-3), (12.12) oxadixyl (77732-09-3), (12.13) oxolinic acid (14698-29-4); (13.1) fenpiclonil (74738-17-3), (13.2) fludioxonil (131341-86-1), (13.3) quinoxyfen (124495-18-7); (14.1) dinocap (131-72-6), (14.2) fluazinam (79622-59-6), (14.3) meptyldinocap (131-72-6), (14.4) binapacryl (485-31-4); (15) Further compounds like for example (15.1) ametoctradin (865318-97-4), (15.2) benthiazole (21564-17-0), (15.3) bethoxazin (163269-30-5), (15.4) carvone (99-49-0), (15.5) chinomethionat (2439-01-2), (15.6) cyflufenamid (180409-60-3), (15.7) cymoxanil (57966-95-7), (15.8) dazomet (533-74-4), (15.9) debacarb (62732-91-6), (15.10) dichlorophen (97-23-4), (15.11) diclomezine (62865-36-5), (15.12) dicloran (99-30-9), (15.13) difenzoquat (43222-48-6), (15.14) diphenylamine (122-39-4), (15.15) ferimzone (89269-64-7), (15.16) flumetover (154025-04-4), (15.17) fluopicolide (239110-15-7), (15.18) fluoroimide (41205-21-4), (15.19) flusulfamide (106917-52-6), (15.20) fosetyl-aluminium (39148-24-8), (15.21) hexachlorobenzene (118-74-1), (15.22) isotianil (224049-04-1), (15.23) methasulfocarb (66952-49-6), (15.24) methyl isothiocyanate (556-61-6), (15.25) metrafenone (220899-03-6), (15.26) nitrothal-isopropyl (10552-74-6), (15.27) octhilinone (26530-20-1), (15.28) oxyfenthiin (34407-87-9), (15.29) propamocarb-fosetylate, (15.30) proquinazid (189278-12-4), (15.31) pyrrolnitrine (1018-71-9), (15.32) quintozene (82-68-8), (15.33) tecloftalam (76280-91-6), (15.34) tecnazene (117-18-0), (15.35) triazoxide (72459-58-6), (15.36) trichlamide (70193-21-4), (15.37) zarilamid (84527-51-5), (15.38) quinolin-8-ol sulfate (2:1) (salt) (8-hydroxyquinoline sulfat) (134-31-6), (15.39) 2,3,5,6-tetrachloro-4-(methylsulfonyl) pyridine (13108-52-6), (15.40) 3,4,5-trichloropyridine-2,6-dicarbonitrile (17824-85-0), (15.41) 3-[5-(4-chlorophenyl)-2,3-dimethylisoxazolidin-3-yl]pyridine, (15.43) 2-butoxy-6-iodo-3-propyl-4H-chromen-4-one, (15.44) N-[1-(5-bromo-3-chloropyridin-2-yl)ethyl]-2,4-dichloropyridine-3-carboxamide, (15.45) N-[(5-bromo-3-chloropyridin-2-yl)methyl]-2,4-dichloropyridine-3-carboxamide, (15.46) N-[1-(5-bromo-3-chloropyridin-2-yl)ethyl]-2-fluoro-4-iodopyridine-3-carboxamide, (15.47) N-(4-chlorobenzyl)-3-[3-methoxy-4-(prop-2-yn-1-yloxy)phenyl]propanamide, (15.48) N-[(4-chlorophenyl)(cyano)methyl]-3-[3-methoxy-4-(prop-2-yn-1-yloxy)phenyl]propanamide, (15.49) S-prop-2-en-1-yl 5-amino-2-(1-methylethyl)-4-(2-methylphenyl)-3-oxo-2,3-dihydro-1H-pyrazole-1-carbothioate, (15.50) 2,3-dibutyl-6-chlorothieno[2,3-d]pyrimidin-4(3H)-one (221451-58-7), (15.51) ethyl (2Z)-3-amino-2-cyano-3-phenylprop-2-enoate, (15.52) 5-amino-1,3,4-thiadiazole-2-thiol, (15.53) 1-[(4-methoxyphenoxy)methyl]-2,2-dimethylpropyl 1H-imidazole-1-carboxylate (111227-17-9), (15.54) 3-chloro-5-(4-chlorophenyl)-4-(2,6-difluorophenyl)-6-methylpyridazine, (15.55) 4-(4-chlorophenyl)-5-(2,6-difluorophenyl)-3,6-dimethylpyridazine, (15.56) tebufloquin (376645-78-2), (15.57) flutianil (304900-25-2), (15.58) (5-bromo-2-methoxy-4-methylpyridin-3-yl)(2,3,4-trimethoxy-6-methylphenyl)methanone (known from EP-A 1 559 320), (15.59) tolnifanide (304911-98-6), (15.60) N-{(Z)-[(cyclopropylmethoxy)imino][6-(difluoromethoxy)-2,3-difluorophenyl]methyl}-2-phenylacetamide (221201-92-9), (15.61) N-{(E)-[(cyclopropylmethoxy)imino][6-(difluoromethoxy)-2,3-difluorophenyl]methyl}-2-phenylacetamide, (15.62) phosphorous acid and its salts (13598-36-2), (15.63) 5-chloro-N'-phenyl-N'-prop-2-yn-1-ylthiophene-2-sulfonohydrazide (134-31-6), (15.64) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.65) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.66) pentyl {6-[({[(1-methyl-1H-tetrazol-5-yl)(phenyl)methylidene]amino}-oxy)methyl]pyridin-2-yl}carbamate, (15.67) capsimycin (70694-08-5), (15.68) chloroneb (2675-77-6), (15.69) cufraneb (11096-18-7), (15.70) cyprosulfamide (221667-31-8), (15.71) difenzoquat methylsulphate (43222-48-6), (15.72) ecomate, (15.73) fosetyl-calcium, (15.74) fosetyl-sodium (39148-16-8), (15.75) irumamycin (81604-73-1), (15.76) mildiomycin (67527-71-3), (15.77) natamycin (7681-93-8), (15.78) nickel dimethyldithiocarbamate (15521-65-0), (15.79) oxamocarb (917242-12-7), (15.80) pentachlorophenol and salts (87-86-5), (15.81) phenazine-1-carboxylic acid, (15.82) phenothrin, (15.83) propanosine-s odium (88498-02-6), (15.84) quinolin-8-ol (134-31-6), (15.85) 2-phenylphenol and salts (90-43-7), (15.86) 5-methyl-6-octyl-3,7-dihydro[1,2,4]triazolo[1,5-a] pyrimidin-7-amine, (15.87) 2-[5-methyl-3-(trifluoro-methyl)-1H-pyrazol-1-yl]-1-(4-{4-[(5R)-5-phenyl-4,5-dihydro-1,2-oxazol-3-yl]-1,3-thiazol-2-yl}piperidin-1-yl) ethanone, (15.88) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]-ethanone and salts thereof.

Particularly preferred combinations and or compositions comprise the amidine of formula (Ia) and at least one insecticidally active compound of group (B-II), which is selected from the group consisting of alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, and xylylcarb; acephate, azamethiphos, azinphos (-methyl, -ethyl), cadusafos, chlorethoxyfos, chlorfenvinphos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon, and vamidothion, chlordane, endosulfan (alpha-); or fiproles (phenylpyrazoles), e.g. ethiprole, fipronil, pyrafluprole, and pyriprole, acrinathrin, allethrin (d-cis-trans, d-trans), bifenthrin, bioallethrin, bioallethrin S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer), prallethrin, profluthrin, pyrethrin (pyrethrum), resmethrin, RU 15525, silafluofen, tefluthrin, tetramethrin [(1R)-isomers)], tralomethrin, transfluthrin and ZXI 8901; or DDT; or methoxychlor, chloronicotinyls, e.g. acetamiprid, clothianidin, dinotefuran, imidacloprid, nitenpyram, thiacloprid, thiamethoxam; or nicotine, spinetoram and spinosad, abamectin, emamectin benzoate, lepimectin, and milbemectin, hydroprene, kinoprene, methoprene; or fenoxycarb; pyriproxyfen, methyl bromide and other alkyl halides, chloropicrin; sulfuryl fluoride; borax; tartar emetic, pymetrozine or flonicamid, clofentezine, diflovidazin, hexythiazox, etoxazole, *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1,diafenthiuron; azocyclotin, cyhexatin, and fenbutatin oxide; propargite; tetradifon, chlorfenapyr, DNOC, bensultap, cartap hydrochloride, thiocyclam, and thiosultap-sodium, bistrifluoron, chlorfluazuron, diflubenzuron, flucycloxuron, flufenoxuron, hexaflumuron, lufenuron, novaluron, noviflumuron, penfluoron, teflubenzuron, and triflumuron, buprofezin, cyromazine, chromafenozide, halofenozide, methoxyfenozide, and tebufenozide, amitraz, hydramethylnon; acequinocyl or fluacrypyrim, fenazaquin, fenpyroximate, pyrimidifen, pyridaben, tebufenpyrad, tolfenpyrad or rotenone, indoxacarb; metaflumizone, spirodiclofen and spiromesifen, spirotetramat, aluminium phosphide, calcium phosphide, phosphine, and zinc phosphide or cyanide, cyenopyrafen, chlorantraniliprole (Rynaxypyr), Cyantraniliprole (Cyazypyr), and flubendiamide, azadirachtin, amidoflumet, benzoximate, bifenazate, chinomethionat, cryolite, cyflumetofen, dicofol, flufenerim, pyridalyl, and pyrifluquinazon, 4-{[(6-bromopyrid-3-yl)methyl](2-fluorethyl)amino}furan-2(5H)-on (known from WO 2007/115644), 4-{[(6-fluoropyrid-3-yl)methyl](2,2-difluorethyl)amino}furan-2(5H)-on (known from WO 2007/115644), 4-{[(2-chlor-1,3-thiazol-5-yl)methyl] (2-fluorethyl)amino}furan-2(5H)-on (known from WO 2007/115644), 4-{[(6-chloropyrid-3-yl)methyl](2-fluorethyl)amino}furan-2(5H)-on (known from WO 2007/115644), 4-{[(6-chloropyrid-3-yl)methyl](2,2-difluorethyl)amino}furan-2(5H)-on known from WO 2007/115644), 4-{[(6-chlor-5-fluoropyrid-3-yl)methyl](methyl)amino}furan-2(5H)-on (known from WO 2007/115643), 4-{[(5,6-dichloropyrid-3-yl)methyl](2-fluorethyl)amino}furan-2(5H)-on (known from WO 2007/115646), 4-{[(6-chlor-5-fluoropyrid-3-yl)methyl] (cyclopropyl)amino}furan-2(5H)-on (known from WO 2007/115643), 4-{[(6-chloropyrid-3-yl)methyl](cyclopropyl)amino}furan-2(5H)-on (known from EP-A-0 539 588), 4-{[(6-chloropyrid-3-yl)methyl](methyl)amino}furan-2(5H)-on (known from EP-A-0 539 588), [(6-chloropyridin-3-yl)methyl](methyl)oxido-λ$^4$-sulfanylidencyanamid (known from WO 2007/149134), [1-(6-chloropyridin-3-yl)ethyl](methyl)oxido-λ$^4$-sulfanylidencyanamid (known from WO 2007/149134) and its diastereomers (A) and (B); [(6-trifluoromethylpyridin-3-yl)methyl](methyl)oxido-λ$^4$-sulfanylidencyanamid (known from WO 2007/095229), or sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), and 1-{2,4-dimethyl-5-[(2,2,2-trifluoroethyl)sulfinyl]phenyl}-3-(trifluoromethyl)-1H-1,2,4-triazole (known from WO 1999/55668), fluensulfone (5-chloro-2-[(3,4,4-trifluorobut-3-en-1-yl)sulfonyl]-1,3-thiazole), 1-[2-fluoro-4-methyl-5-[(2,2,2-trifluoroethyl)sulfinyl]phenyl]-3-(trifluoromethyl)-1H-1,2,4-Triazol-5-amine (bekannt aus WO 2006/043635), [(3S,4aR,12R,12aS,12bS)-3-[(Cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methylcyclopropancarboxylat (bekannt aus WO 2006/129714), 2-Cyan-3-(difluoromethoxy)-N,N-dimethylbenzolsulfonamid (bekannt aus WO2006/056433), 2-Cyan-3-(difluoromethoxy)-N-methylbenzolsulfonamid (bekannt aus WO2006/100288), 2-Cyan-3-(difluoromethoxy)-N-ethylbenzolsulfonamid (bekannt aus WO2005/035486), 4-(Difluoromethoxy)-N-ethyl-N-methyl-1,2-benzothiazol-3-amin-1,1-dioxid (bekannt aus WO2007/057407), N-[1-(2,3-Dimethylphenyl)-2-(3,5-dimethylphenyl)ethyl]-4,5-dihydro-1,3-thiazol-2-amin (bekannt aus WO2008/104503) furthermore products based on *Bacillus firmus* (I-1582, BioNeem, Votivo).

Particularly preferred combinations and or compositions comprise the amidine of formula (Ia) and at least one plant growth regulating compound of group (B-III), which is selected from the group consisting of clofibrin [2-(4-chlorophenoxy)-2-methylpropionic acid], 2,3,5-tri-iodobenzoic acid, 4-CPA (4-chlorophenoxyacetic acid), 2,4-D (2,4-dichlorophenoxyacetic acid), 2,4-DB [4-(2,4-dichlorophenoxy)butyric acid], 2,4-DEP {tris[2-(2,4-dichlorophenoxy)ethyl]phosphite}, dichlorprop, fenoprop, IAA (β-indoleacetic acid), IBA (4-indol-3-ylbutyric acid), naphthaleneacetamide, α-naphthaleneacetic acid, 1-naphthol, naphthoxyacetic acid, potassium naphthenate, sodium naphthenate, 2,4,5-T [(2,4,5-trichlorophenoxy)acetic acid], 2iP [N-(3-methylbut-2-enyl)-1H-purine-6-amine], benzyladenine, kinetin, zeatin, calcium cyanamide, dimethipin, endothal, ethephon, merphos, metoxuron, pentachlorophenol, thidiazuron, tribufos, aviglycine, aviglycine-hydrochloride, 1-methylcyclopropen, ACC (1-aminocyclopropancarboxylic acid), etacelasil, ethephon, glyoxime, gibberellines A1, A4, A7, gibberellinic acid (=gibberellin A3), abscisinic acid, ancymidol, butralin, carbaryl, chlorphonium or its chloride, chlorpropham, dikegulac, dikegulac-sodium, flumetralin, fluoridamide, fosamine, glyphosine, isopyrimol, jasmonic acid, maleic acid hydrazide or its potassium salt, mepiquat or its chloride, piproctanyl or its bromide, prohydrojasmon, propham, 2,3,5-tri-iodobenzoic acid, 2,6-diisopropylnaphthaline, cloprop, 1-naphthylacetic acid ethylester, isoprothiolane, MCPB-ethyl [4-(4-Cchloro-o-tolyloxy)butyric acid ethylester], N-acetylthiazolidine-4-carboxylic acid, n-decanol, pelargonic acid, N-phenylphthaliminic acid, tecnazene, triacontanol, 2,3-dihydro-5,6-diphenyl-1,4-oxathiin, 2-cyano-3-(2,4-dichlorophenyl)acrylic acid, 2-hydrazinoethanol, alorac, amidochlor, BTS 44584 [dimethyl(4-piperidinocarbonyloxy-2,5-xylyl)sulfonium-toluen-4-sulfonat], chloramben, chlorfluren, chlorfluren-methyl, dicamba-methyl, dichlorflurenol, dichlorflurenol-methyl, dimexano, etacelasil, hexafluoraceton-trihydrat, N-(2-ethyl-2H-pyrazol-3-yl)-N'-phenylurea, N-m-tolylphthalaminic acid, N-Pyrrolidinosuccinaminic acid, 3-tert-Butylphenoxyacetic acid propylester, pydanon, sodium (Z)-3-chloroacrylate, chlorfluren, chloroflurenol, chloroflurenol-methyl, dichlorflurenol, fluorenol, chlormequat, chlormequat-chlorid, daminozide, flurprimidol, mefluidide, mefluidide-diolamin, paclobutrazol, cyproconazole, tetcyclacis, uniconazole, uniconazole-P, brassinolides, forchlorfenuron, hymexazol, 2-amino-6-oxypurine derivatives, indolinon derivatives, 3,4-disubstituted maleimide derivatives and azepinon derivatives, benzofluor, buminafos, carvone, ciobutide, clofencet, clofence-potassium, cloxyfonac, cloxyfonac-Natrium, cyclanilide, cycloheximide, epocholeone, ethychlozate, ethylene, fenridazon, heptopargil, holosulf, inabenfide, karetazan, leadarsenate, methasulfocarb, prohexadione, prohexadione-Calcium, pydanon, sintofen, triapenthenol, trinexapac and trinexapac-ethyl.

In conjunction with the present invention compounds (A) and (B-I) to (B-III) are different from each other.

In the combinations according to the invention the compounds A and B are present in a synergistically effective weight ratio of A:B in a range of 100:1 to 1:100, preferably in a weight ratio of 50:1 to 1:50, most preferably in a weight ratio of 20:1 to 1:20. Further ratios of A:B which can be used according to the present invention with increasing preference in the order given are: 1000:1 to 1:1000, 750:1 to 1:750, 500:1 to 1:500, 400:1 to 1:400, 300:1 to 1:300, 250:1 to 1:250, 200:1 to 1:250, 175:1 to 1:175, 150:1 to 1:150, 125:1 to 1:125, 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) can be present in tautomeric form, such a compound is understood hereinabove and hereinbelow also to include, where applicable, corresponding tautomeric forms, even when these are not specifically mentioned in each case.

Compounds (A) or compounds (B) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. Compounds (A) or compounds (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propylamine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compounds (A) or the compounds (B) in free foil and in the form of their salts, hereinabove and herein below any reference to the free compounds (A) or free compounds (B) or to their salts should be understood as including also the corresponding salts or the free compounds (A) or free compounds (B), respectively, where appropriate and expedient. The equivalent also applies to tautomers of compounds (A) or compounds (B) and to their salts or stereoisomers.

According to the invention the expression "combination" stands for the various combinations of compounds (A) and (B), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds (A) and (B) is not essential for working the present invention.

In a further aspect there is provided a composition comprising a combination according to this invention. A composition comprises at least one compound (A) according to formula (I) and one compound (B) as defined above. Preferably the fungicidal composition comprises an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilizers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Colouring agents such as inorganic pigments, for example iron oxide, titanium oxide, ferrocyanblue, and organic pigments such as alizarin, azo and metallophthalocyanine dyes, and trace elements such as iron, manganese, boron, copper, cobalt, molybdenum and zinc salts can be used.

Optionally, other additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compounds, preferably from 10 to 70% by weight.

The combination or composition according to the invention can be used as such, in form of their formulations or as the use forms prepared therefrom, such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

The treatment of plants and plant parts with the active compound combination or composition according to the invention is carried out directly or by action on their environment, habitat or storage area by means of the normal treatment methods, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting.

These active compound combinations or compositions include not only compositions which are ready to be applied to the plant or seed to be treated by means of a suitable device, such as a spraying or dusting device, but also concentrated commercial compositions which must be diluted before application to the crop.

The active compounds within the composition according to the invention have potent fungicidal activity and can be employed for controlling undesired fungi in crop protection or in the protection of materials.

Within the active compound combinations or compositions according to the invention, fungicide compounds can be employed in crop protection for example for controlling fungi being Plasmodiophoromycetes, Oomycetes, Chytridiomycetes, Zygomycetes, Ascomycetes, Basidiomycetes and Deuteromycetes.

The active compound combination or composition according to the invention can be used to curatively or preventively control the phytopathogenic fungi of plants or reducing the mycotoxin contamination of plant or plant material. Thus, according to a further aspect of the invention, there is provided a method for curatively or preventively controlling the phytopathogenic fungi of plants or reducing the mycotoxin contamination of plant or plant parts comprising the use of a composition according to the invention by application to the seed, the plant or to the fruit of the plant or to the soil in which the plant is growing or in which it is desired to grow.

The active compound combination or composition of the invention is also suitable for the treatment of seeds. A large part of the damage caused by fungi on cultigens occurs by infestation of the seed during storage and after sowing the seed in the ground as well as during and after germination of the plants. This phase is especially critical since the roots and shoots of the growing plant are particularly sensitive and even a small amount of damage can lead to withering of the whole plant.

In a particular embodiment of the invention plant or plant has at least 10% less mycotoxin, more preferable at least 20% mycotoxin, more preferable at least 40% mycotoxin, more preferable at least 50% mycotoxin, more preferable at least 80% mycotoxin contamination than plant or plant material which has not been treated.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

By plant parts is meant all above ground and below ground parts and organs of plants such as shoot, leaf, flower, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners, tubers, grains, and seeds also belong to plant parts Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak choi, kohlrabi, radish, horseradish, cress, Chinese cabbage), Leguminosae sp. (for instance peanuts, peas and beans beans—such as climbing beans and broad beans), Chenopodiaceae sp. (for instance mangold, spinach beet, spinach, beetroots), Asteraceae sp. (for instance sunflower), Brassicaceae sp. (for instance white cabbage, red cabbage, broccoli, cauliflower, brussel sprouts, pak choi, kohlrabi, radish as well as canola, rapeseed, mustard, horseradish, cress), (Cruciferae sp. (for instance colza), Fabacae sp. (for instance peanuts and beans), Papilionaceae sp. (for instance soybean), Solanaceae sp. (for instance potatoes), Malvaceae (for instance okra), Asparagaceae (for instance asparagus); horticultural and forest crops; ornamental plants; as well as genetically modified homologues of these crops.

According to the invention all cereal, nut, fruit and spice plants are comprised, in particular cereals like all wheat species, rye, barley, triticale, rice, sorghum, oats, millets, quinoa, buckwheat, fonio, amaranth, teff and durum; in particular fruits of various botanical taxa such as Rosaceae sp. (for instance pip fruit such as apples and pears, but also stone fruit such as apricots, cherries, almonds and peaches, berry fruits such as strawberries), *Vitis* sp. (for instance *Vitis vinifera*: grape vine, raisins), Manihoteae sp. (for instance *Manihot esculenta*, manioc), *Theobroma* sp. (for instance *Theobroma cacao*: cocoa), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp.; in particular nuts of various botanical taxa such as peanuts, Juglandaceae sp. (Walnut, Persian Walnut (*Juglans regia*), Butternut (*Juglans*), Hickory, Shagbark Hickory, Pecan (*Carya*), Wingnut (*Pterocarya*)), Fagaceae sp. (Chestnut (*Castanea*), Chestnuts, including Chinese Chestnut, Malabar chestnut, Sweet Chestnut, Beech (*Fagus*), Oak (*Quercus*), Stone-oak, Tanoak (*Lithocarpus*)); Betulaceae sp. (Alder (*Alnus*), Birch (*Betula*), Hazel, Filbert (*Corylus*), Hornbeam), Leguminosae sp. (for instance peanuts, peas and beans beans—such as climbing beans and broad beans), Asteraceae sp. (for instance sunflower seed), Almond, Beech, Butternut, Brazil nut, Candlenut, Cashew, Colocynth, Cotton seed, *Cucurbita ficifolia*, Filbert, Indian Beech or Pongam Tree, Kola nut, Lotus seed, Macadamia, Mamoncillo, Maya nut, Mongongo, Oak acorns, Ogbono nut, Paradise nut, Pili nut, Pine nut, Pistacchio, Pumpkin seed, water Caltrop; soybeans (*Glycine* sp., *Glycine max*); in particular spices like Ajwain (*Trachyspermum ammi*), Allspice (*Pimenta dioica*), Alkanet (*Anchusa arvensis*), Amchur—mango powder (*Mangifera*), Angelica (*Angelica archangelica*), Anise (*Pimpinella anisum*), Aniseed myrtle (*Syzygium anisatum*), Annatto (*Bixa orellana* L.), Apple mint (*Mentha suaveolens*), *Artemisia vulgaris*/Mugwort, Asafoetida (*Ferula assafoetida*), Berberis, Banana, Basil (*Ocimum basilicum*), Bay leaves, Bistort (*Persicaria bistorta*"), Black cardamom, Black cumin, Blackcurrant, Black limes, Bladder wrack (*Fucus vesiculosus*), Blue Cohosh, Blue-leaved Mallee (*Eucalyptus polybractea*), Bog Labrador Tea (*Rhododendron groenlandicum*), Boldo (*Peumus boldus*), Bolivian Coriander (*Porophyllum ruderale*), Borage (*Borago officinalis*), Calamus, Calendula, Calumba (*Jateorhiza calumba*), Chamomile, Candle nut, Cannabis, Caper (*Capparis spinosa*), Caraway, Cardamom, Carob Pod, *Cassia*, Casuarina, Catnip, Cat's Claw, Catsear, Cayenne pepper, *Celastrus Paniculatus*—Herb., Celery salt, Celery seed, Centaury, Chervil (*Anthriscus cerefolium*), Chickweed, Chicory, Chile pepper, Chili powder, Cinchona, Chives (*Allium schoenoprasum*), Cicely (*Myrrhis odorata*), Cilantro (see Coriander) (*Coriamirum sativum*), Cinnamon (and *Cassia*), Cinnamon Myrtle (*Backhousia myrtifolia*), Clary, Cleavers, Clover, Cloves, Coffee, Coltsfoot, Comfrey, Common Rue, Condurango, Coptis, Coriander, Costmary (*Tanacetum balsamita*), Couchgrass, Cow Parsley (*Anthriscus sylvestris*), Cowslip, Cramp Bark (*Viburnum opulus*), Cress, Cuban Oregano (*Plectranthus amboinicus*), Cudweed, Cumin, Curry leaf (*Murraya koenigii*), Damiana (*Turnera aphrodisiaca, T. diffusa*), Dandelion (*Taraxacum officinale*), Demulcent, Devil's claw (*Harpagophytum procumbens*), Dill seed, Dill (*Anethum graveolens*), Dorrigo Pepper (*Tasmannia stipitata*), Echinacea Echinopanax Elatum, Edelweiss, Elderberry, Elderflower, Elecampane, *Eleutherococcus senticosus*, Emmenagogue, Epazote (*Chenopodium ambrosioides*), Ephedra-, *Eryngium foetidum*, Eucalyptus, Fennel (*Foeniculum vulgare*), Fenugreek, Feverfew, Figwort, Filé powder, Five-spice powder (Chinese), Fo-ti-tieng, Fumitory, Galangal, Garam masala, Garden cress, Garlic chives, Garlic, Ginger (*Zingiber officinale*), *Ginkgo biloba, Ginseng, Ginseng, Siberian (Eleutherococcus senticosus*), Goat's Rue (*Galega officinalis*), Goada masala, Golden Rod, Golden Seal, Gotu Kola, Grains of paradise (*Aframomum melegueta*), Grains of Sam (*Xylopia aethiopica*), Grape seed extract, Green tea, Ground Ivy, Guaco, Gypsywort, Hawthorn (*Crataegus sanguinea*), Hawthorne Tree, Hemp, Herbes de Provence, *Hibiscus*, Holly, Holy Thistle, Hops, Horehound, Horseradish, Horsetail (*Equisetum telmateia*), Hyssop (*Hyssopus officinalis*), Jalap, Jasmine, Jiaogulan (*Gynostemma pentaphyllum*), Joe Pye weed (Gravelroot), John the Conqueror, Juniper, Kaffir Lime Leaves (*Citrus hystrix, C. papedia*), Kaala masala, Knotweed, Kokam, Labrador tea, Lady's Bedstraw, Lady's Mantle, Land cress, Lavender (*Lavandula* spp.), Ledum, Lemon Balm (*Melissa Officinalis*), Lemon basil, Lemongrass (*Cymbopogon citratus, C. flexuosus*, and other species), Lemon Ironbark (*Eucalyptus staigeriana*), Lemon mint, Lemon Myrtle (*Backhousia citriodora*), Lemon Thyme, Lemon verbena (*Lippia citriodora*), Licorice—adaptogen, Lime Flower, *Limnophila aromatica*, Lingzhi, Linseed, Liquorice, Long pepper, Lovage (*Levisticum officinale*), Luohanguo, Mace, Mahlab, Malabathrum, Manchurian Thorn Tree (*Aralia manchurica*)]], Mandrake, Marjoram (*Origanum majorana*), *Marrubium vulgare*, Marsh Labrador Tea, Marshmallow, Mastic, Meadowsweet, Mei Yen, Melegueta pepper (*Aframomum melegueta*), Mint (*Mentha* spp.), Milk thistle (*Silybum*), Bergamot (*Monarda didyma*), Motherwort, Mountain Skullcap, Mullein (*Verbascum thapsus*), Mustard, Mustard seed, *Nashia inaguensis*, Neem, *Nepeta*, Nettle, *Nigella sativa, Nigella* (Kolanji, Black caraway), Noni, Nutmeg (and Mace) Marijuana, *Oenothera* (*Oenothera biennis* et al), Olida (*Eucalyptus olida*), Oregano (*Origanum vulgare, O. heracleoticum*, and other species), Orris root, Osmorhiza, Olive Leaf (used in tea and as herbal supplement), *Panax quinquefolius*, Pandan leaf, Paprika, Parsley (*Petroselinum crispum*), Passion Flower, Patchouli, Pennyroyal, Pepper (black, white, and green), Peppermint, Peppermint Gum (Eucalyptus dives), *Perilla*, Plantain, Pomegranate, Ponch phoran, Poppy seed, Primrose (*Primula*)—candied flowers, tea, *Psyllium*, Purslane, *Quassia*, Quatre epices, Ramsons, Ras el-hanout, Raspberry (leaves), Reishi, Restharrow, *Rhodiola rosea*, Riberry (*Syzygium luehmannii*), Rocket/Arugula, Roman chamomile, Rooibos, Rosehips, Rosemary (*Rosmarinus officinalis*), Rowan Berries, Rue, Safflower, Saffron, Sage (*Salvia officinalis*), Saigon Cinnamon, St John's Wort, Salad Burnet (*Sanguisorba minor* or *Poterium sanguisorba*), Salvia, Sichuan Pepper (Sansho), *Sassafras*, Savory (*Satureja hortensis*, S. Montana), *Schisandra* (*Schisandra chinensis*), *Scutellaria costaricana*, Senna (herb), *Senna obtusifolia*, Sesame seed, Sheep Sorrel, Shepherd's Purse, Sialagogue, Siberian Chaga, Siberian ginseng (*Eleutherococcus senticosus*), *Siraitia grosvenorii* (luohanguo), Skullcap, Sloe Berries, Smudge Stick, Sonchus, Sorrel (*Rumex* spp.), Southernwood, Spearmint, Speedwell, Squill, Star anise, Stevia, Strawberry Leaves, Suma (*Pfaffia paniculata*), Sumac, Summer savory, *Sutherlandia frutescens*, Sweet grass, Sweet cicely (*Myrrhis odorata*), Sweet woodruff, Szechuan pepper (*Xanthoxylum piperitum*), Tacamahac, Tamarind, Tandoori masala, Tansy, Tarragon (*Artemisia dracunculus*), Tea, *Teucrium polium*, That basil, Thistle, Thyme, Toor Dall, Tormentil, *Tribulus terrestris*, Tulsi (*Ocimum tenuiflorum*), Turmeric (*Curcuma longa*), Uva Ursi also known as Bearberry, *Vanilla* (*Vanilla planifolia*), Vasaka, Vervain, Vetiver, Vietnamese Coriander (*Persicaria odorata*), Wasabi (*Wasabia japonica*), Watercress, Wattleseed, Wild ginger, Wild Lettuce, Wild thyme, Winter savory, Witch Hazel, Wolfberry, Wood Avens, Wood Betony, Woodruff, Wormwood, Yarrow, Yerba Buena, Yohimbe, Za'atar, Zedoary Root.

The method of treatment according to the invention is used in the treatment of plants. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, homologous recombination methods, molecular or genetic markers or by bioengineering and genetic engineering methods methods or marker-assisted breeding methods, for example SMART breeding ("Selection with Markers and Advanced Reproductive Technologies"). Plants can also be genetically modified organisms (GMOs). Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co-suppression technology or RNA interference—RNAi—technology). A heterologous gene that is located in the genome is also called a transgene. A transgene that is defined by its particular location in the plant genome is called a transformation or transgenic event.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp, the genes encoding a Petunia EPSPS, a Tomato EPSPS, or an *Eleusine* EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034; or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) secreted protein from *Bacillus thuringiensis* or *Bacillus cereus* which is insecticidal in the presence of a second secreted protein from *Bacillus thuringiensis* or B. cereus, such as the binary toxin made up of the VIP1A and VIP2A proteins; or 7) hybrid insecticidal protein comprising parts from different secreted proteins from *Bacillus thuringiensis* or *Bacillus cereus*, such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants b. plants which contain a stress tolerance enhancing transgene capable of reducing the expression and/or the activity of the PARG encoding genes of the plants or plants cells.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase.

Further particularly genetically modified plants include plants containing a gene in an agronomically neutral or beneficial position as described by the event listed in Table A

TABLE A

| Event | Company | Description | Crop |
|---|---|---|---|
| ASR368 | Scotts Seeds | Glyphosate tolerance derived by inserting a modified 5-enolpyruvylshikimate-3-phosphate synthase (EPSPS) encoding gene from *Agrobacterium tumefaciens*, parent line B99061 | *Agrostis stolonifera* Creeping Bentgrass |
| H7-1 | Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. | *Beta vulgaris* |
| T120-7 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Beta vulgaris* |
| GTSB77 | Novartis Seeds; Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. | *Beta vulgaris* sugar Beet |
| 23-18-17, 23-198 | Monsanto Company (formerly Calgene) | High laurate (12:0) and myristate (14:0) canola produced by inserting a thioesterase encoding gene from the California bay laurel (*Umbellularia californica*). | *Brassica napus* (Argentine Canola) |
| 45A37, 46A40 | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. | *Brassica napus* (Argentine Canola) |

TABLE A-continued

| Event | Company | Description | Crop |
|---|---|---|---|
| 46A12, 46A16 | Pioneer Hi-Bred International Inc. | Combination of chemical mutagenesis, to achieve the high oleic acid trait, and traditional breeding with registered canola varieties. | *Brassica napus* (Argentine Canola) |
| GT200 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) |
| GT73, RT73 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) |
| HCN10 | Aventis CropScience | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| HCN92 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| MS1, RF1 => PGS1 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| MS1, RF2 => PGS2 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| MS8 x RF3 | Bayer CropScience (Aventis CropScience(AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. | *Brassica napus* (Argentine Canola) |
| OXY-235 | Aventis CropScience (formerly Rhone Poulenc Inc.) | Tolerance to the herbicides bromoxynil and ioxynil by incorporation of the nitrilase gene from *Klebsiella pneumoniae*. | *Brassica napus* (Argentine Canola) |
| PHY14, PHY35 | Aventis CropScience (formerly Plant Genetic Systems) | Male sterility was via insertion of the barnase ribonuclease gene from Bacillus amyloliquefaciens; fertility restoration by insertion of the barstar RNase inhibitor; PPT resistance was via PPT-acetyltransferase (PAT) from *Streptomyces hygroscopicus*. | *Brassica napus* (Argentine Canola) |
| PHY36 | Aventis CropScience (formerly Plant Genetic Systems) | Male sterility was via insertion of the barnase ribonuclease gene from Bacillus amyloliquefaciens; fertility restoration by insertion of the barstar RNase inhibitor; PPT resistance was via PPT-acetyltransferase (PAT) from *Streptomyces hygroscopicus*. | *Brassica napus* (Argentine Canola) |
| T45 (HCN28) | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| HCR-1 | Bayer CropScience (Aventis CropScience(AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. | *Brassica rapa* (Polish Canola) |
| ZSR500/502 | Monsanto Company | Introduction of a modified 5-enol-pyruvylshikimate-3-phosphate synthase (EPSPS) and a gene from Achromobacter sp that degrades glyphosate by conversion to aminomethylphosphonic acid (AMPA) and glyoxylate by interspecific crossing with GT73. | *Brassica rapa* (Polish Canola) |

TABLE A-continued

| Event | Company | Description | Crop |
|---|---|---|---|
| 55-1/63-1 | Cornell University | Papaya ringspot virus (PRSV) resistant papaya produced by inserting the coat protein (CP) encoding sequences from this plant potyvirus. | *Carica papaya* (Papaya) |
| RM3-3, RM3-4, RM3-6 | Bejo Zaden BV | Male sterility was via insertion of the barnase ribonuclease gene from Bacillus amyloliquefaciens; PPT resistance was via the bar gene from *S. hygroscopicus*, which encodes the PAT enzyme. | *Cichorium intybus* (Chicory) |
| A, B | Agritope Inc. | Reduced accumulation of S-adenosylmethionine (SAM), and consequently reduced ethylene synthesis, by introduction of the gene encoding S-adenosylmethionine hydrolase. | *Cucumis melo* (Melon) |
| CZW-3 | Asgrow (USA); Seminis Vegetable Inc. (Canada) | Cucumber mosiac virus (CMV), zucchini yellows mosaic (ZYMV) and watermelon mosaic virus (WMV) 2 resistant squash (*Curcurbita pepo*) produced by inserting the coat protein (CP) encoding sequences from each of these plant viruses into the host genome. | *Cucurbita pepo* (Squash) |
| ZW20 | Upjohn (USA); Seminis Vegetable Inc. (Canada) | Zucchini yellows mosaic (ZYMV) and watermelon mosaic virus (WMV) 2 resistant squash (*Curcurbita pepo*) produced by inserting the coat protein (CP) encoding sequences from each of these plant potyviruses into the host genome. | *Cucurbita pepo* (Squash) |
| 66 | Florigene Pty Ltd. | Delayed senescence and sulfonylurea herbicide tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulfonyl urea herbicides was via the introduction of a chlorsulfuron tolerant version of the acetolactate synthase (ALS) encoding gene from tobacco. | *Dianthus caryophyllus* (Carnation) |
| 4, 11, 15, 16 | Florigene Pty Ltd. | Modified colour and sulfonylurea herbicide tolerant carnations produced by inserting two anthocyanin biosynthetic genes whose expression results in a violet/mauve colouration. Tolerance to sulfonyl urea herbicides was via the introduction of a chlorsulfuron tolerant version of the acetolactate synthase (ALS) encoding gene from tobacco. | *Dianthus caryophyllus* (Carnation) |
| 959A, 988A, 1226A, 1351A, 1363A, 1400A | Florigene Pty Ltd. | Introduction of two anthocyanin biosynthetic genes to result in a violet/mauve colouration; Introduction of a variant form of acetolactate synthase (ALS). | *Dianthus caryophyllus* (Carnation) |
| A2704-12, A2704-21, A5547-35 | Aventis CropScience | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| A5547-127 | Bayer CropScience (Aventis Crop Science(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| DP356043 | Pioneer Hi-Bred International Inc. | Soybean event with two herbicide tolerance genes: glyphosate N-acetyltransferase, which detoxifies glyphosate, and a modified acetolactate synthase (A | *Glycine max* L. (Soybean) |
| G94-1, G94-19, G168 | DuPont Canada Agricultural Products | High oleic acid soybean produced by inserting a second copy of the fatty acid desaturase (GmFad2-1) encoding gene from soybean, which resulted in "silencing" of the endogenous host gene. | *Glycine max* L. (Soybean) |
| GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. | *Glycine max* L. (Soybean) |
| GU262 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4. | *Glycine max* L. (Soybean) |
| OT96-15 | Agriculture & Agri-Food Canada | Low linolenic acid soybean produced through traditional cross-breeding to incorporate the novel trait from a naturally occurring fan1 gene mutant that was selected for low linolenic acid. | *Glycine max* L. (Soybean) |
| W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus*. | *Glycine max* L. (Soybean) |
| 15985 | Monsanto Company | Insect resistant cotton derived by transformation of the DP50B parent variety, which contained event 531 (expressing Cry1Ac protein), with purified plasmid DNA | *Gossypium hirsutum* L. (Cotton) |

TABLE A-continued

| Event | Company | Description | Crop |
|---|---|---|---|
| | | containing the cry2Ab gene from *B. thuringiensis* subsp. *kurstaki*. | |
| 19-51A | DuPont Canada Agricultural Products | Introduction of a variant form of acetolactate synthase (ALS). | *Gossypium hirsutum L.* (*Cotton*) |
| 281-24-236 | DOW AgroSciences LLC | Insect-resistant cotton produced by inserting the cry1F gene from *Bacillus thuringiensis* var. *aizawai*. The PAT encoding gene from *Streptomyces viridochromogenes* was introduced as a selectable marker. | *Gossypium hirsutum L.* (Cotton) |
| 3006-210-23 | DOW AgroSciences LLC | Insect-resistant cotton produced by inserting the cry1Ac gene from *Bacillus thuringiensis* subsp. *kurstaki*. The PAT encoding gene from *Streptomyces viridochromogenes* was introduced as a selectable marker. | *Gossypium hirsutum L.* (Cotton) |
| 31807/31808 | Calgene Inc. | Insect-resistant and bromoxynil herbicide tolerant cotton produced by inserting the cry1Ac gene from *Bacillus thuringiensis* and a nitrilase encoding gene from *Klebsiella pneumoniae*. | *Gossypium hirsutum L.* (Cotton) |
| BXN | Calgene Inc. | Bromoxynil herbicide tolerant cotton produced by inserting a nitrilase encoding gene from *Klebsiella pneumoniae*. | *Gossypium hirsutum L.* (*Cotton*) |
| COT102 | Syngenta Seeds, Inc. | Insect-resistant cotton produced by inserting the vip3A(a) gene from *Bacillus thuringiensis* AB88. The APH4 encoding gene from *E. coli* was introduced as a selectable marker. | *Gossypium hirsutum L.* (Cotton) |
| DAS-21Ø23-5 × DAS-24236-5 | DOW AgroSciences LLC | WideStrike ™, a stacked insect-resistant cotton derived from conventional cross-breeding of parental lines 3006-210-23 (OECD identifier: DAS-21Ø23-5) and 281-24-236 (OECD identifier: DAS-24236-5). | *Gossypium hirsutum L.* (Cotton) |
| DAS-21Ø23-5 × DAS-24236-5 × MON88913 | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). | *Gossypium hirsutum L.* (Cotton) |
| DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). | *Gossypium hirsutum L.* (Cotton) |
| LLCotton25 | Bayer CropScience (Aventis CropScience(AgrEvo)) | Glufosinate ammonium herbicide tolerant cotton produced by inserting a modified phosphinothricin acetyltransferase (PAT) encoding gene from the soil bacterium *Streptomyces hygroscopicus*. | *Gossypium hirsutum L.* (Cotton) |
| LLCotton25 × MON15985 | Bayer CropScience (Aventis CropScience(AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) | *Gossypium hirsutum L.* (Cotton) |
| GBH614 | Bayer CropScience (Aventis CropScience(AgrEvo)) | Glyphosate herbicide tolerant cotton produced by inserting 2mepsps gene into variety Coker312 by Agrobacterium under the control of Ph4a748At and TPotpC | *Gossypium hirsutum L.* (Cotton) |
| MON1445/1698 | Monsanto Company | Glyphosate herbicide tolerant cotton produced by inserting a naturally glyphosate tolerant form of the enzyme 5-enolpyruvyl shikimate-3-phosphate synthase (EPSPS) from *A. tumefaciens* strain CP4. | *Gossypium hirsutum L.* (Cotton) |
| MON15985 × MON88913 | Monsanto Company | Stacked insect resistant and glyphosate tolerant cotton produced by conventional cross-breeding of the parental lines MON88913 (OECD identifier: MON-88913-8) and 15985 (OECD identifier: MON-15985-7). Glyphosate tolerance is derived from MON88913 which contains two genes encoding the enzyme 5-enolypyruvylshikimate-3-phosphate synthase (EPSPS) from the CP4 strain of *Agrobacterium tumefaciens*. Insect resistance is derived MON15985 which was produced by transformation of the DP50B parent variety, which contained event 531 (expressing Cry1Ac protein), with purified plasmid DNA containing the cry2Ab gene from *B. thuringiensis* subsp. *kurstaki*. | *Gossypium hirsutum L.* (Cotton) |
| MON-15985-7 × MON-Ø1445-2 | Monsanto Company | Stacked insect resistant and herbicide tolerant cotton derived from conventional cross-breeding of the parental lines 15985 (OECD identifier: MON-15985-7) and MON1445 (OECD identifier: MON-Ø1445-2). | *Gossypium hirsutum L.* (Cotton) |
| MON531/757/1076 | Monsanto Company | Insect-resistant cotton produced by inserting the cry1Ac gene from *Bacillus thuringiensis* subsp. *kurstaki* HD-73 (B.t.k.). | *Gossypium hirsutum L.* (Cotton) |
| MON88913 | Monsanto Company | Glyphosate herbicide tolerant cotton produced by inserting two genes encoding the enzyme 5-enolypyruvylshikimate-3-phosphate synthase (EPSPS) from the CP4 strain of *Agrobacterium tumefaciens*. | *Gossypium hirsutum L.* (Cotton) |

TABLE A-continued

| Event | Company | Description | Crop |
|---|---|---|---|
| MON-ØØ531-6 × MON-Ø1445-2 | Monsanto Company | Stacked insect resistant and herbicide tolerant cotton derived from conventional cross-breeding of the parental lines MON531 (OECD identifier: MON-ØØ531-6) and MON1445 (OECD identifier: MON-Ø1445-2). | *Gossypium hirsutum* L. (Cotton) |
| X81359 | BASF Inc. | Tolerance to imidazolinone herbicides by selection of a naturally occurring mutant. | *Helianthus annuus* (Sunflower) |
| RH44 | BASF Inc. | Selection for a mutagenized version of the enzyme acetohydroxyacid synthase (AHAS), also known as acetolactate synthase (ALS) or acetolactate pyruvate-lyase. | *Lens culinaris* (Lentil) |
| FP967 | University of Saskatchewan, Crop Dev. Centre | A variant form of acetolactate synthase (ALS) was obtained from a chlorsulfuron tolerant line of *A. thaliana* and used to transform flax. | *Linum usitatissimum* L. (Flax, Linseed) |
| 5345 | Monsanto Company | Resistance to lepidopteran pests through the introduction of the cry1Ac gene from *Bacillus thuringiensis* subsp. *kurstaki*. | *Lycopersicon esculentum* (Tomato) |
| 8338 | Monsanto Company | Introduction of a gene sequence encoding the enzyme 1-amino-cyclopropane-1-carboxylic acid deaminase (ACCd) that metabolizes the precursor of the fruit ripening hormone ethylene. | *Lycopersicon esculentum* (Tomato) |
| 1345-4 | DNA Plant Technology Corporation | Delayed ripening tomatoes produced by inserting an additional copy of a truncated gene encoding 1-aminocyclopropane-1-carboxyllic acid (ACC) synthase, which resulted in downregulation of the endogenous ACC synthase and reduced ethylene accumulation. | *Lycopersicon esculentum* (Tomato) |
| 35 1 N | Agritope Inc. | Introduction of a gene sequence encoding the enzyme S-adenosylmethionine hydrolase that metabolizes the precursor of the fruit ripening hormone ethylene | *Lycopersicon esculentum* (Tomato) |
| B, Da, F | Zeneca Seeds | Delayed softening tomatoes produced by inserting a truncated version of the polygalacturonase (PG) encoding gene in the sense or anti-sense orientation in order to reduce expression of the endogenous PG gene, and thus reduce pectin degradation. | *Lycopersicon esculentum* (Tomato) |
| FLAVR SAVR | Calgene Inc. | Delayed softening tomatoes produced by inserting an additional copy of the polygalacturonase (PG) encoding gene in the anti-sense orientation in order to reduce expression of the endogenous PG gene and thus reduce pectin degradation. | *Lycopersicon esculentum* (Tomato) |
| J101, J163 | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. | *Medicago sativa* (Alfalfa) |
| C/F/93/08-02 | Societe National d'Exploitation des Tabacs et Allumettes | Tolerance to the herbicides bromoxynil and ioxynil by incorporation of the nitrilase gene from *Klebsiella pneumoniae*. | *Nicotiana tabacum* L. (Tobacco) |
| Vector 21-41 | Vector Tobacco Inc. | Reduced nicotine content through introduction of a second copy of the tobacco quinolinic acid phosphoribosyltransferase (QTPase) in the antisense orientation. The NPTII encoding gene from *E. coli* was introduced as a selectable marker to identify transformants. | *Nicotiana tabacum* L. (Tobacco) |
| CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) |
| IMINTA-1, IMINTA-4 | BASF Inc. | Tolerance to imidazolinone herbicides induced by chemical mutagenesis of the acetolactate synthase (ALS) enzyme using sodium azide. | *Oryza sativa* (Rice) |
| LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*). | *Oryza sativa* (Rice) |
| LLRICE601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*). | *Oryza sativa* (Rice) |
| C5 | United States Department of Agriculture—Agricultural Research Service | Plum pox virus (PPV) resistant plum tree produced through *Agrobacterium*-mediated transformation with a coat protein (CP) gene from the virus. | *Prunus domestica* (Plum) |
| PWC16 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) |
| ATBT04-6, ATBT04-27, ATBT04-30, ATBT04-31, ATBT04-36, SPBT02-5, SPBT02-7 | Monsanto Company | Colorado potato beetle resistant potatoes produced by inserting the cry3A gene from *Bacillus thuringiensis* (subsp. *Tenebrionis*). | *Solanum tuberosum* L. (Potato) |

TABLE A-continued

| Event | Company | Description | Crop |
|---|---|---|---|
| BT6, BT10, BT12, BT16, BT17, BT18, BT23 | Monsanto Company | Colorado potato beetle resistant potatoes produced by inserting the cry3A gene from *Bacillus thuringiensis* (subsp. *Tenebrionis*). | *Solanum tuberosum* L. (Potato) |
| RBMT15-101, SEMT15-02, SEMT15-15 | Monsanto Company | Colorado potato beetle and potato virus Y (PVY) resistant potatoes produced by inserting the cry3A gene from *Bacillus thuringiensis* (subsp. Tenebrionis) and the coat protein encoding gene from PVY. | *Solanum tuberosum* L. (Potato) |
| RBMT21-129, RBMT21-350, RBMT22-082 | Monsanto Company | Colorado potato beetle and potato leafroll virus (PLRV) resistant potatoes produced by inserting the cry3A gene from *Bacillus thuringiensis* (subsp. *Tenebrionis*) and the replicase encoding gene from PLRV. | *Solanum tuberosum* L. (Potato) |
| AP205CL | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| AP602CL | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| BW255-2, BW238-3 | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| BW7 | BASF Inc. | Tolerance to imidazolinone herbicides induced by chemical mutagenesis of the acetohydroxyacid synthase (AHAS) gene using sodium azide. | *Triticum aestivum* (Wheat) |
| MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. | *Triticum aestivum* (Wheat) |
| SWP965001 | Cyanamid Crop Protection | Selection for a mutagenized version of the enzyme acetohydroxyacid synthase (AHAS), also known as acetolactate synthase (ALS) or acetolactate pyruvate-lyase. | *Triticum aestivum* (Wheat) |
| Teal 11A | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) |
| 176 | Syngenta Seeds, Inc. | Insect-resistant maize produced by inserting the cry1Ab gene from *Bacillus thuringiensis* subsp. *kurstaki*. The genetic modification affords resistance to attack by the European corn borer (ECB). | *Zea mays* L. (Maize) |
| 3751IR | Pioneer Hi-Bred International Inc. | Selection of somaclonal variants by culture of embryos on imidazolinone containing media. | *Zea mays* L. (Maize) |
| 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. | *Zea mays* L. (Maize) |
| ACS-ZMØØ3-2 × MON-ØØ81Ø-6 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). | *Zea mays* L. (Maize) |
| B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. | *Zea mays* L. (Maize) |
| BT11 (X4334CBR, X4734CBR) | Syngenta Seeds, Inc. | Insect-resistant and herbicide tolerant maize produced by inserting the cry1Ab gene from *Bacillus thuringiensis* subsp. *kurstaki*, and the phosphinothricin N-acetyltransferase (PAT) encoding gene from *S. viridochromogenes*. | *Zea mays* L. (Maize) |
| BT11 × MIR604 | Syngenta Seeds, Inc. | Stacked insect resistant and herbicide tolerant maize produced by conventional cross breeding of parental lines BT11 (OECD unique identifier: SYN-BTØ11-1) and MIR604 (OECD unique identifier: SYN-IR6Ø5-5). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. | *Zea mays* L. (Maize) |
| BT11 × MIR604 × GA21 | Syngenta Seeds, Inc. | Stacked insect resistant and herbicide tolerant maize produced by conventional cross breeding of parental lines BT11 (OECD unique identifier: SYN-BØ11-1), MIR604 (OECD unique identifier: SYN-IR6Ø5-5) and GA21 (OECD unique identifier: MON-ØØØ21-9). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from | *Zea mays* L. (Maize) |

TABLE A-continued

| Event | Company | Description | Crop |
|---|---|---|---|
| | | *S. viridochromogenes*. Corn rootworm-resistance is derived from MIR604 which contains the mcry3A gene from *Bacillus thuringiensis*. Tolerance to glyphosate herbcicide is derived from GA21 which contains a a modified EPSPS gene from maize. | |
| CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. | *Zea mays* L. (Maize) |
| DAS-06275-8 | DOW AgroSciences LLC | Lepidopteran insect resistant and glufosinate ammonium herbicide-tolerant maize variety produced by inserting the cry1F gene from *Bacillus thuringiensis* var aizawai and the phosphinothricin acetyltransferase (PAT) from *Streptomyces hygroscopicus*. | *Zea mays* L. (Maize) |
| DAS-59122-7 | DOW AgroSciences LLC and Pioneer Hi-Bred International Inc. | Corn rootworm-resistant maize produced by inserting the cry34Ab1 and cry35Ab1 genes from *Bacillus thuringiensis* strain PS149B1. The PAT encoding gene from *Streptomyces viridochromogenes* was introduced as a selectable marker. | *Zea mays* L. (Maize) |
| DAS-59122-7 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Tolerance to glyphosate herbcicide is derived from NK603. | *Zea mays* L. (Maize) |
| DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-Ø15Ø7-1) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Lepidopteran resistance and toleraance to glufosinate ammonium herbicide is derived from TC1507. Tolerance to glyphosate herbcicide is derived from NK603. | *Zea mays* L. (Maize) |
| DAS-Ø15Ø7-1 × MON-ØØ6Ø3-6 | DOW AgroSciences LLC | Stacked insect resistant and herbicide tolerant corn hybrid derived from conventional cross-breeding of the parental lines 1507 (OECD identifier: DAS-Ø15Ø7-1) and NK603 (OECD identifier: MON-ØØ6Ø3-6). | *Zea mays* L. (Maize) |
| DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* | *Zea mays* L. (Maize) |
| DK404SR | BASF Inc. | Somaclonal variants with a modified acetyl-CoA-carboxylase (ACCase) were selected by culture of embryos on sethoxydim enriched medium. | *Zea mays* L. (Maize) |
| Event 3272 | Syngenta Seeds, Inc. | Maize line expressing a heat stable alpha-amylase gene amy797E for use in the dry-grind ethanol process. The phosphomannose isomerase gene from *E. coli* was used as a selectable marker. | *Zea mays* L. (Maize) |
| EXP1910IT | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). | *Zea mays* L. (Maize) |
| GA21 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | *Zea mays* L. (Maize) |
| IT | Pioneer Hi-Bred International Inc. | Tolerance to the imidazolinone herbicide, imazethapyr, was obtained by in vitro selection of somaclonal variants. | *Zea mays* L. (Maize) |
| LY038 | Monsanto Company | Altered amino acid composition, specifically elevated levels of lysine, through the introduction of the cordapA gene, derived from *Corynebacterium glutamicum*, encoding the enzyme dihydrodipicolinate synthase (cDHDPS). | *Zea mays* L. (Maize) |
| MIR604 | Syngenta Seeds, Inc. | Corn rootworm resistant maize produced by transformation with a modified cry3A gene. The phosphomannose isomerase gene from *E. coli* was used as a selectable marker. | *Zea mays* L. (Maize) |
| MIR604 × GA21 | Syngenta Seeds, Inc. | Stacked insect resistant and herbicide tolerant maize produced by conventional cross breeding of parental lines MIR604 (OECD unique identifier: SYN-IR6Ø5-5) and GA21 (OECD unique identifier: MON-ØØØ21-9). Corn | *Zea mays* L. (Maize) |

TABLE A-continued

| Event | Company | Description | Crop |
|---|---|---|---|
| | | rootworm-resistance is derived from MIR604 which contains the mcry3A gene from *Bacillus thuringiensis*. Tolerance to glyphosate herbcicide is derived from GA21. | |
| MON80100 | Monsanto Company | Insect-resistant maize produced by inserting the cry1Ab gene from *Bacillus thuringiensis* subsp. *kurstaki*. The genetic modification affords resistance to attack by the European corn borer (ECB). | *Zea mays* L. (Maize) |
| MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. | *Zea mays* L. (Maize) |
| MON809 | Pioneer Hi-Bred International Inc. | Resistance to European corn borer (*Ostrinia nubilalis*) by introduction of a synthetic cry1Ab gene. Glyphosate resistance via introduction of the bacterial version of a plant enzyme, 5-enolpyruvyl shikimate-3-phosphate synthase (EPSPS). | *Zea mays* L. (Maize) |
| MON810 | Monsanto Company | Insect-resistant maize produced by inserting a truncated form of the cry1Ab gene from *Bacillus thuringiensis* subsp. *kurstaki* HD-1. The genetic modification affords resistance to attack by the European corn borer (ECB). | *Zea mays* L. (Maize) |
| MON810 × MON88017 | Monsanto Company | Stacked insect resistant and glyphosate tolerant maize derived from conventional cross-breeding of the parental lines MON810 (OECD identifier: MON-ØØ81Ø-6) and MON88017 (OECD identifier: MON-88Ø17-3). European corn borer (ECB) resistance is derived from a truncated form of the cry1Ab gene from *Bacillus thuringiensis* subsp. *kurstaki* HD-1 present in MON810. Corn rootworm resistance is derived from the cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. | *Zea mays* L. (Maize) |
| MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. | *Zea mays* L. (Maize) |
| MON863 | Monsanto Company | Corn root worm resistant maize produced by inserting the cry3Bb1 gene from *Bacillus thuringiensis* subsp. *kumamotoensis*. | *Zea mays* L. (Maize) |
| MON88017 | Monsanto Company | Corn rootworm-resistant maize produced by inserting the cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4. | *Zea mays* L. (Maize) |
| MON89034 | Monsanto Company | Maize event expressing two different insecticidal proteins from *Bacillus thuringiensis* providing resistance to number of lepidopteran pests. | *Zea mays* L. (Maize) |
| MON89034 × MON88017 | Monsanto Company | Stacked insect resistant and glyphosate tolerant maize derived from conventional cross-breeding of the parental lines MON89034 (OECD identifier: MON-89Ø34-3) and MON88017 (OECD identifier: MON-88Ø17-3). Resistance to Lepiopteran insects is derived from two crygenes present in MON89043. Corn rootworm resistance is derived from a single cry genes and glyphosate tolerance is derived from the 5-enolpyruvylshikimate-3-phosphate synthase (EPSPS) encoding gene from *Agrobacterium tumefaciens* present in MON88017. | *Zea mays* L. (Maize) |
| MON-ØØ6Ø3-6 × MON-ØØ81Ø-6 | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). | *Zea mays* L. (Maize) |
| MON-ØØ81Ø-6 × LY038 | Monsanto Company | Stacked insect resistant and enhanced lysine content maize derived from conventional cross-breeding of the parental lines MON810 (OECD identifier: MON-ØØ81Ø-6) and LY038 (OECD identifier: REN-ØØØ38-3). | *Zea mays* L. (Maize) |
| MON-ØØ863-5 × MON-ØØ6Ø3-6 | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). | *Zea mays* L. (Maize) |
| MON-ØØ863-5 × MON-ØØ81Ø-6 | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) | *Zea mays* L. (Maize) |

TABLE A-continued

| Event | Company | Description | Crop |
|---|---|---|---|
| MON-ØØ863-5 × MON-ØØ81Ø-6 × MON-ØØ6Ø3-6 | Monsanto Company | Stacked insect resistant and herbicide tolerant corn hybrid derived from conventional cross-breeding of the stacked hybrid MON-ØØ863-5 × MON-ØØ81Ø-6 and NK603 (OECD identifier: MON-ØØ6Ø3-6). | *Zea mays* L. (Maize) |
| MON-ØØØ21-9 × MON-ØØ81Ø-6 | Monsanto Company | Stacked insect resistant and herbicide tolerant corn hybrid derived from conventional cross-breeding of the parental lines GA21 (OECD identifider: MON-ØØØ21-9) and MON810 (OECD identifier: MON-ØØ81Ø-6). | *Zea mays* L. (Maize) |
| MS3 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | *Zea mays* L. (Maize) |
| MS6 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | *Zea mays* L. (Maize) |
| NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | *Zea mays* L. (Maize) |
| SYN-BTØ11-1 × MON-ØØØ21-9 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). | *Zea mays* L. (Maize) |
| T14, T25 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. | *Zea mays* L. (Maize) |
| TC1507 | Mycogen (c/o Dow AgroSciences); Pioneer (c/o Dupont) | Insect-resistant and glufosinate ammonium herbicide tolerant maize produced by inserting the cry1F gene from *Bacillus thuringiensis* var. *aizawai* and the phosphinothricin N-acetyltransferase encoding gene from *Streptomyces viridochromogenes*. | *Zea mays* L. (Maize) |
| TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due the presence of the cry1F gene from *Bacillus thuringiensis* var. *aizawai*. Corn rootworm-resistance is derived from DAS-59122-7 which contains the cry34Ab1 and cry35Ab1 genes from *Bacillus thuringiensis* strain PS149B1. Tolerance to glufosinate ammonium herbcicide is derived from TC1507 from the phosphinothricin N-acetyltransferase encoding gene from *Streptomyces viridochromogenes*. | *Zea mays* L. (Maize) |
| DP-Ø981 4Ø-6 (Event 98140) | Pioneer Hi-Bred International Inc. | Corn line 98140 was genetically engineered to express the GAT4621 (glyphosate acetyltransferase) and ZM-HRA (modified version of a maize acetolactate synthase) proteins. The GAT4621 protein, encoded by the gat4621 gene, confers tolerance to glyphosate-containing herbicides by acetylating glyphosate and thereby rendering it non-phytotoxic. The ZM-HRA protein, encoded by the zm-hra gene, confers tolerance to the ALS-inhibiting class of herbicides. | *Zea mays* L. (Maize) |

A further aspect of the instant invention is a method of protecting natural substances of vegetable or animal origin or their processed forms, which have been taken from the natural life cycle, which comprises applying to said natural substances of vegetable or animal origin or their processed forms a combination of compounds (A) and (B) in a synergistically effective amount.

A preferred embodiment is a method of protecting natural substances of vegetable origin or their processed forms, which have been taken from the natural life cycle, which comprises applying to said natural substances of vegetable origin or their processed forms a combination of compounds (A) and (B) in a synergistically effective amount.

A further preferred embodiment is a method of protecting fruit, preferably pomes, stone fruits, soft fruits and citrus fruits, or their processed forms, which have been taken from the natural life cycle, which comprises applying to said natural substances of vegetable origin or their processed forms a combination of compounds (A) and (B) in a synergistically effective amount.

The combinations or compositions of the present invention may also be used in the field of protecting technical material against attack of fungi. According to the instant invention, the term "technical material" includes paper; carpets; constructions; cooling and heating systems; wall-boards; ventilation and air conditioning systems and the like. The combinations according the present invention can prevent disadvantageous effects such as decay, discoloration or mold. Preferably "storage goods" is understood to denote wall-boards.

The method of treatment according to the invention can also be used in the field of protecting storage goods against attack of fungi. According to the instant invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

In another preferred embodiment of the invention "storage goods" is understood to denote wood. The fungicide combination or composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

Numerous fungi are serious pests of economically important agricultural crops. Further, crop contamination by fungal toxins is a major problem for agriculture throughout the world.

Mycotoxins, such as aflatoxins, ochratoxins, patulin, fumonisins, zearalenones, and trichothecenes, are toxic fungal metabolites, often found in agricultural products that are characterized by their ability to cause health problems for humans and vertebrates. They are produced for example by different *Fusarium* and *Aspergillus, Penicillium* and *Alternaria* species.

Aflatoxins are toxins produced by *Aspergillus* species that grow on several crops, in particular on maize or corn before and after harvest of the crop as well as during storage. The biosynthesis of aflatoxins involves a complex polyketide pathway starting with acetate and malonate. One important intermediate is sterigmatocystin and O-methylsterigmatocystin which are direct precursors of aflatoxins. Important producers of aflatoxins are *Aspergillus flavus*, most strains of *Aspergillus parasiticus, Aspergillus nomius, Aspergillus bombycis, Aspergillus pseudotamarii, Aspergillus ochraceoroseus, Aspergillus rambelli, Emericella astellata, Emericella venezuelensis, Bipolaris* spp., *Chaetomium* spp., *Farrowia* spp., and *Monocillium* spp., in particular *Aspergillus flavus* and *Aspergillus parasiticus* (Plant Breeding (1999), 118, pp 1-16). There are also additional *Aspergillus* species known. The group of aflatoxins consists of more than 20 different toxins, in particular aflatoxin B1, B2, G1 and G2, cyclopiazonic acid (CPA).

Ochratoxins are mycotoxins produced by some *Aspergillus* species and *Penicilium* species, like *A. ochraceus, A. carbonarius* or *P. viridicatum*, Examples for Ochratoxins are ochratoxin A, B, and C. Ochratoxin A is the most prevalent and relevant fungal toxin of this group.

Fumonisins are toxins produced by *Fusarium* species that grow on several crops, mainly corn, before and after harvest of the crop as well as during storage. The diseases, *Fusarium* kernel, ear and stalk rot of corn, is caused by *Fusarium verticillioides, F. subglutinans, F. moniliforme*, and *F. proliferatum*. The main mycotoxins of these species are the fumonisins, of which more than ten chemical forms have been isolated. Examples for fumonisins are FB1, FB2 and FB3. In addition the above mentioned *Fusarium* species of corn can also produce the mycotoxins moniliformin and beauvericin. In particular *Fusarium* verticillioides is mentioned as an important pathogen of corn, this *Fusarium* species produces as the main mycotoxin fumonisins of the B-type.

Trichothecenes are those mycotoxins of primary concern which can be found in *Fusarium* diseases of small grain cereals like wheat, barley, rye, triticale, rice, sorghum and oat. They are sesquiterpene epoxide mycotoxins produced by species of *Fusarium, Trichothecium*, and *Myrothecium* and act as potent inhibitors of eukaryotic protein synthesis.

Some of these trichothecene producing *Fusarium* species also infect corn or maize Examples of trichothecene mycotoxins include T-2 toxin, HT-2 toxin, isotrichodermol, DAS, 3-deacetylcalonectrin, 3,15-dideacetylcalonectrin, scirpentriol, neosolaniol; 15-acetyldeoxynivalenol, 3-acetyldeoxynivalenol, nivalenol, 4-acetylnivalenol (fusarenone-X), 4,15-diacetylnivalenol, 4,7,15-acetylnivalenol, and deoxynivalenol (hereinafter "DON") and their various acetylated derivatives. The most common trichothecene in *Fusarium* head blight is DON produced for example by *Fusarium graminearum* and *F. culmorum*.

Another mycotoxin mainly produced by *F. culmorum, F. graminearum* and *F. cerealis* is zearalenone, a phenolic resorcyclic acid lactone that is primarily an estrogenic fungal metabolite.

*Fusarium* species that produce mycotoxins, such as fumonisins and trichothecenes, include *F. acuminatum, F. crookwellense, F., verticillioides, F. culmorum, F. avenaceum, F. equiseti, F. moniliforme, F, graminearum (Gibberella zeae), F. lateritium, F. poae, F. sambucinum (G. pulicaris), F. proliferatum, F. subglutinans, F. sporotrichioides* and other *Fusarium* species.

In contrast the species *Microdochium nivale* also a member of the so-called *Fusarium* complex is known to not produce any mycotoxins.

Both acute and chronic mycotoxicoses in farm animals and in humans have been associated with consumption of wheat, rye, barley, oats, rice and maize contaminated with *Fusarium* species that produce trichothecene mycotoxins. Experiments with chemically pure trichothecenes at low dosage levels have reproduced many of the features observed in moldy grain toxicoses in animals, including anemia and immunosuppression, hemorrhage, emesis and feed refusal. Historical and epidemiological data from human populations indicate an association between certain disease epidemics and consumption of grain infected with *Fusarium* species that produce trichothecenes. In particular, outbreaks of a fatal disease known as alimentary toxic aleukia, which has occurred in Russia since the nineteenth century, have been associated with consumption of over-wintered grains contaminated with *Fusarium* species that produce the trichothecene T-2 toxin. In Japan, outbreaks of a similar disease called akakabi-byo or red mold disease have been associated with grain infected with *Fusarium* species that produce the trichothecene, DON. Trichothecenes were detected in the toxic grain samples responsible for recent human disease outbreaks in India and Japan. There exists, therefore, a need for agricultural methods for preventing, and crops having reduced levels of, mycotoxin contamination.

Further, mycotoxin-producing *Fusarium* species are destructive pathogens and attack a wide range of plant species. The acute phytotoxicity of mycotoxins and their occurrence in plant tissues also suggests that these mycotoxins play a role in the pathogenesis of *Fusarium* on plants. This implies that mycotoxins play a role in disease and, therefore, reducing their toxicity to the plant may also prevent or reduce disease in the plant. Further, reduction in disease levels may have the additional benefit of reducing mycotoxin contamination on the plant and particularly in grain where the plant is a cereal plant.

Among the diseases of plants or crops that can be controlled by the method according to the invention, mention may be made of:

Powdery Mildew Diseases such as

*Blumeria* diseases caused for example by *Blumeria graminis*
*Podosphaera* diseases caused for example by *Podosphaera leucotricha*
*Sphaerotheca* diseases caused for example by *Sphaerotheca fuliginea*
*Uncinula* diseases caused for example by *Uncinula necator*

Rust Diseases such as

*Gymnosporangium* diseases caused for example by *Gymnosporangium sabinae*

*Hemileia* diseases caused for example by *Hemileia vastatrix*

*Phakopsora* diseases caused for example by *Phakopsora pachyrhizi* and *Phakopsora meibomiae*

*Puccinia* diseases caused for example by *Puccinia recondite*, and *Puccinia triticina;*

*Uromyces* diseases caused for example by *Uromyces appendiculatus*

Oomycete Diseases such as

*Bremia* diseases caused for example by *Bremia lactucae*

Peronospora diseases caused for example by *Peronospora pisi* and *Peronospora brassicae*

*Phytophthora* diseases caused for example by *Phytophthora infestans*

*Plasmopara* diseases caused for example by *Plasmopara viticola*

*Pseudoperonospora* diseases caused for example by *Pseudoperonospora humuli* and *Pseudoperonospora cubensis*

*Pythium* diseases caused for example by *Pythium ultimum*

Leafspot, Leaf blotch and Leaf Blight Diseases such as

*Alternaria* diseases caused for example by *Alternaria solani*

*Cercospora* diseases caused for example by *Cercospora beticola*

*Cladiosporium* diseases caused for example by *Cladiosporium cucumerinum*

*Cochliobolus* diseases caused for example by *Cochliobolus sativus* (Conidiaform: *Drechslera*, Syn: *Helminthosporium*);

*Colletotrichum* diseases caused for example by *Colletotrichum lindemuthianum*

*Cycloconium* diseases caused for example by *Cycloconium oleaginum*

*Diaporthe* diseases caused for example by *Diaporthe citri*

*Elsinoe* diseases caused for example by *Elsinoe fawcettii*

*Gloeosporium* diseases caused for example by *Gloeosporium laeticolor*

*Glomerella* diseases caused for example by *Glomerella cingulata*

*Guignardia* diseases caused for example by *Guignardia bidwellii*

*Leptosphaeria* diseases caused for example by *Leptosphaeria maculans*

*Magnaporthe* diseases caused for example by *Magnaporthe grisea*

*Mycosphaerella* diseases caused for example by *Mycosphaerella graminicola* and *Mycosphaerella fijiensis*

*Phaeosphaeria* diseases caused for example by *Phaeosphaeria nodorum*

*Pyrenophora* diseases caused for example by *Pyrenophora teres*

*Ramularia* diseases caused for example by *Ramularia collo-cygni*

*Rhynchosporium* diseases caused for example by *Rhynchosporium secalis*

*Septoria* diseases caused for example by *Septoria apii;*

*Typhula* diseases caused for example by *Thyphula incarnata*

*Venturia* diseases caused for example by *Venturia inaequalis*

Root- and Stem Diseases such as

*Corticium* diseases caused for example by *Corticium graminearum*

*Fusarium* diseases caused for example by *Fusarium oxysporum*

*Gaeumannomyces* diseases caused for example by *Gaeumannomyces graminis*

*Rhizoctonia* diseases caused for example by *Rhizoctonia solani*

*Oculimacula* (*Tapesia*) diseases caused for example by *Oculimacula Tapesia acuformis*

*Thielaviopsis* diseases caused for example by *Thielaviopsis basicola*

Ear and Panicle Diseases including Maize cob such as

*Alternaria* diseases caused for example by *Alternaria* spp.

*Aspergillus* diseases caused for example by *Aspergillus flavus*

*Cladosporium* diseases caused for example by *Cladiosporium cladosporioides*

*Claviceps* diseases caused for example by *Claviceps purpurea*

*Fusarium* diseases caused for example by *Fusarium culmorum*

*Gibberella* diseases caused for example by *Gibberella zeae*

*Monographella* diseases caused for example by *Monographella nivalis*

Smut- and Bunt Diseases such as

*Sphacelotheca* diseases caused for example by *Sphacelotheca reiliana*

*Tilletia* diseases caused for example by *Tilletia caries*

*Urocystis* diseases *Urocystis occulta*

*Ustilago* diseases caused for example by *Ustilago nuda;*

Fruit Rot and Mould Diseases such as

*Aspergillus* diseases caused for example by *Aspergillus flavus*

*Botrytis* diseases caused for example by *Botrytis cinerea*

*Penicillium* diseases caused for example by *Penicillium expansum* and *Penicillium purpurogenum*

*Sclerotinia* diseases caused for example by *Sclerotinia sclerotiorum;*

*Verticillium* diseases caused for example by *Verticillium alboatrum*

Seed- and Soilborne Decay, Mould, Wilt, Rot and Damping-off diseases

*Fusarium* diseases caused for example by *Fusarium culmorum*

*Phytophthora* diseases caused for example by *Phytophthora cactorum*

*Pythium* diseases caused for example by *Pythium ultimum*

*Rhizoctonia* diseases caused for example by *Rhizoctonia solani*

*Sclerotium* diseases caused for example by *Sclerotium rolfsii*
Canker, Broom and Dieback Diseases such as
*Nectria* diseases caused for example by *Nectria galligena*
Blight Diseases such as
*Monilinia* diseases caused for example by *Monilinia laxa*
Leaf Blister or Leaf Curl Diseases including deformation of blooms and fruits such as *Taphrina* diseases caused for example by *Taphrina deformans*
Decline Diseases of Wooden Plants such as
Esca disease caused for example by *Phaeomoniella clamydospora* and *Phaeoacremonium aleophilum* and *Fomitiporia mediterranea*
Diseases of Flowers and Seeds such as
*Botrytis* diseases caused for example by *Botrytis cinerea*
Diseases of Tubers such as
*Rhizoctonia* diseases caused for example by *Rhizoctonia solani*
*Helminthosporium* diseases caused for example by *Helminthosporium solani*
Diseases caused by Bacterial Organisms such as
*Xanthomonas* species for example *Xanthomonas campestris* pv. *Oryzae*
Pseudomonas species for example *Pseudomonas syringae* pv. *Lachrymans*
*Erwinia* species for example *Erwinia amylovora*.

The active compound combinations or compositions related to this invention are preferably used to control the following diseases:

*Aspergillus flavus*, most strains of *Aspergillus parasiticus, Aspergillus nomius, Aspergillus bombycis, Aspergillus pseudotamarii, Aspergillus ochraceoroseus, Aspergillus rambelli, Emericella astellata, Emericella venezuelensis, Bipolaris* spp., *Chaetomium* spp., *Farrowia* spp., and *Monocillium* spp., in particular *Aspergillus flavus* and *Aspergillus parasiticus, Fusarium graminearum, Fusarium culmorum, Fusarium cerealis Fusarium acuminatum, Fusarium crookwellense, Fusarium verticillioides, Fusarium culmorum, Fusarium avenaceum, Fusarium equiseti, Fusarium moniliforme, Fusarium graminearum (Gibberella zeae), Fusarium lateritium, Fusarium poae, Fusarium sambucinum (G. pulicaris), Fusarium proliferatum, Fusarium subglutinans, Fusarium* sporotrichioides and other *Fusarium* species.

The method of treatment according to the invention also provides the use of compounds (A) and (B) in a simultaneous, separate or sequential manner.

The dose of active compound usually applied in the method of treatment according to the invention is generally and advantageously for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 2 to 200 g per 100 kilogram of seed, preferably from 3 to 150 g per 100 kilogram of seed;

for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The compounds or mixtures according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

Treatment of Seeds

The invention comprises a procedure in which the seed is treated at the same time with a compound of Group (A) and a compound selected from group (B). It further comprises a method in which the seed is treated with compound of Group (A) and a compound selected from group (B) separately.

The invention also comprises a seed, which has been treated with a compound of Group (A) and a compound selected from group (B) at the same time. The invention also comprises a seed, which has been treated with a compound of Group (A) and a compound selected from group (B) separately. For the latter seed, the active ingredients can be applied in separate layers. These layers can optionally be separated by an additional layer that may or may not contain an active ingredient.

The mixtures of the invention are particularly suitable for the treatment of seeds. A large part of the damage caused by pests on cultigens occurs by infestation of the seed during storage and after sowing the seed in the ground as well as during and after germination of the plants. This phase is especially critical since the roots and shoots of the growing plant are particularly sensitive and even a small amount of damage can lead to withering of the whole plant. There is therefore considerable interest in protecting the seed and the germinating plant by the use of suitable agents.

The control of pests by treatment of the seeds of plants has been known for a considerable time and is the object of continuous improvement. However, there are a number of problems in the treatment of seed that cannot always be satisfactorily solved. Therefore it is worthwhile to develop methods for the protection of seeds and germinating plants which makes the additional application of plant protection agents after seeding or after germination of the plants superfluous. It is further worthwhile to optimize the amount of the applied active material such that the seed and the gelininating plants are protected against infestation by pests as best as possible without the plants themselves being damaged by the active compound applied. In particular, methods for the treatment seed should also take into account the intrinsic insecticidal properties of transgenic plants in order to achieve optimal protection of the seed and germinating plants with a minimal expenditure of plant protection agents.

The present invention relates therefore especially to a method for the protection of seed and germinating plants from infestation with pests in that the seed is treated with the combination/composition of the invention. In addition the invention relates also to the use of the combination/composition of the invention for the treatment seed for protection of the seed and the germinating plants from pests. Furthermore the invention relates to seed which was treated with an combination/composition of the invention for protection from pests.

One of the advantages of the invention is because of the special systemic properties of the combination/composition of the invention treatment with these combination/composition protects not only the seed itself from pests but also the plants emerging after sprouting. In this way the direct treatment of the culture at the time of sowing or shortly thereafter can be omitted.

A further advantage is the synergistic increase in insecticidal activity of the combination/composition of the invention in comparison to the respective individual active compounds, which extends beyond the sum of the activity of both individually applied active compounds. In this way an optimization of the amount of active compound applied is made possible.

It is also be regarded as advantageous that the mixtures of the invention can also be used in particular with transgenic seeds whereby the plants emerging from this seed are capable of the expression of a protein directed against pests. By treatment of such seed with the agents of the invention certain pests can already be controlled by expression of the, for example, insecticidal protein, and it is additionally surprising that a synergistic activity supplementation occurs with the agents of the invention, which improves still further the effectiveness of the protection from pest infestation.

The agents of the invention are suitable for the protection of seed of plant varieties of all types as already described which are used in agriculture, in greenhouses, in forestry, in garden construction or in vineyards. In particular, this concerns seed of maize, peanut, canola, rape, poppy, olive, coconut, cacao, soy, cotton, beet, (e.g. sugar beet and feed beet), rice, millet, wheat, barley, oats, rye, sunflower, sugar cane or tobacco. The combination/compositions of the invention are also suitable for the treatment of the seed of fruit plants and vegetables as previously described. Particular importance is attached to the treatment of the seed of maize, soy, cotton, wheat and canola or rape.

As already described, the treatment of transgenic seed with a combination/composition of the invention is of particular importance. This concerns the seeds of plants which generally contain at least one heterologous gene that controls the expression of a polypeptide with special insecticidal properties. The heterologous gene in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed that contains at least one heterologous gene that originates from *Bacillus* sp. and whose gene product exhibits activity against the European corn borer and/or western corn rootworm. Particularly preferred is a heterologous gene that originates from *Bacillus thuringiensis*.

Within the context of the present invention the combination/composition of the invention is applied to the seed alone or in a suitable formulation. Preferably the seed is handled in a state in which it is so stable, that no damage occurs during treatment. In general treatment of the seed can be carried out at any time between harvest and sowing. Normally seed is used that was separated from the plant and has been freed of spadix, husks, stalks, pods, wool or fruit flesh. Use of seed that was harvested, purified, and dried to moisture content of below 15% w/w. Alternatively, seed treated with water after drying and then dried again can also be used.

In general care must be taken during the treatment of the seed that the amount of the combination/composition of the invention and/or further additive applied to the seed is so chosen that the germination of the seed is not impaired and the emerging plant is not damaged. This is to be noted above all with active compounds which can show phytotoxic effects when applied in certain amounts.

The combination/compositions of the invention can be applied directly, that is without containing additional components and without being diluted. It is normally preferred to apply the combination/composition to the seed in the form of a suitable formulation. Suitable formulations and methods for seed treatment are known to the person skilled in the art.

According to another aspect of the present invention, in the combination or composition according to the invention, the compound ratio A/B may be advantageously chosen so as to produce a synergistic effect. The term synergistic effect is understood to mean in particular that defined by Colby in an article entitled "Calculation of the synergistic and antagonistic responses of herbicide combinations" Weeds, (1967), 15, pages 20-22.

The latter article mentions the formula:

$$E = X + Y - \frac{XY}{100}$$

wherein E represents the expected percentage of inhibition of the pest for the combination of the two compounds at defined doses (for example equal to x and y respectively), X is the percentage of inhibition observed for the pest by compound (A) at a defined dose (equal to x), Y is the percentage of inhibition observed for the pest by compound (B) at a defined dose (equal to y). When the percentage of inhibition observed for the combination is greater than E, there is a synergistic effect.

The term "synergistic effect" also means the effect defined by application of the Tammes method, "Isoboles, a graphic representation of synergism in pesticides", Netherlands Journal of Plant Pathology, 70 (1964), pages 73-80.

BIOLOGICAL EXAMPLES

Here, the efficacy is determined in %. 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

The invention is illustrated by the examples below. However, the invention is not limited to the examples.

Example A

*Pyrenophora teres*-Test (Barley)/Preventive

Solvent: 49 parts by weight of n,n-dimethylacetamid

Emulsifier: 1 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Pyrenophora teres*. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the control, while an efficacy of 100% means that no disease is observed.

TABLE A

Pyrenophora teres-test (barley)/preventive

| Active compounds | Ratio of mixture | Application rate of active compound in g/ha | Efficacy in % found* | calc.** |
|---|---|---|---|---|
| Compound (I-a) | | 62.5 | 40 | |
| 1.41 (Prothioconazole) | | 125 | 70 | |
| I-a + 1.41 | 1:2 | 62.5 + 125 | 100 | 82 |

*found = activity found
**calc. = activity calculated using Colby's formula

Example B

Blumeria Test (Barley)/Preventive

Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are dusted with spores of Blumeria graminis f.sp. hordei.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

TABLE B

Blumeria-test (barley)/preventive

| Active compounds | Ratio of mixture | Application rate of active compound in g/ha | Efficacy in % found* | calc.** |
|---|---|---|---|---|
| Compound (I-a) | | 62.5 | 40 | |

TABLE B-continued

| | Blumeria-test (barley)/preventive | | | |
|---|---|---|---|---|
| | | Application rate of active compound in | Efficacy in % | |
| Active compounds | Ratio of mixture | g/ha | found* | calc.** |
| 3.17 (Trifloxystrobin) 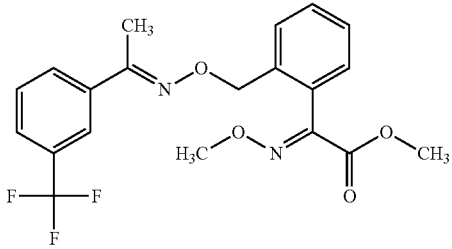 | | 62,5 | 80 | |
| I-a + 3.17 | 1:1 | 62,5 + 62,5 | 100 | 88 |

*found = activity found
**calc. = activity calculated using Colby's formula

TABLE C

| | Blumeria-test (barley)/preventive | | | |
|---|---|---|---|---|
| | | Application rate of active compound in | Efficacy in % | |
| Active compounds | Ratio of mixture | g/ha | found* | calc.** |
| Compound (I-a) | | 62,5 | 40 | |
| 2.2 (Bixafen) | | 62,5 | 10 | |
| I-a + 2.2 | 1:1 | 62,5 + 62,5 | 100 | 46 |

*found = activity found
**calc. = activity calculated using Colby's formula

The invention claimed is:
1. A composition comprising
(A) at least one compound according to formula (I)

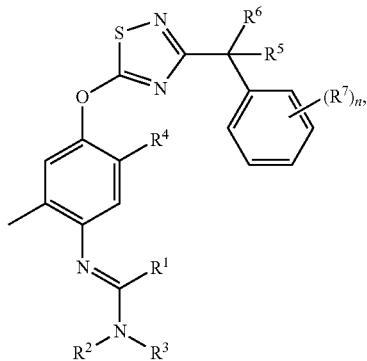

wherein
$R^1$ is selected from the group consisting of hydrogen, mercapto (—SH), and methyl;
$R^2$ is selected from the group consisting of methyl and ethyl;
$R^3$ is selected from the group consisting of methyl, ethyl, and isopropyl;
or alternatively $R^2$ and $R^3$ form, together with the N-atom to which they are attached, a piperidyl, a pyrrolidyl or a 2,6-dimethylmorpholinyl ring;
$R^4$ is selected from the group consisting of chlorine, fluorine, trifluoromethyl, difluoromethyl and methyl;
$R^5$ and $R^6$ independently from each other, are selected from the group consisting of hydrogen, methyl and ethyl; or form, together with the C-atom to which they are attached, a cyclopropyl ring;
$R^7$ is selected from the group consisting of chlorine, tert-butyl, methoxy, ethoxy, trimethylsilyl and triethylsilyl;
n is 1
or salts or stereoisomers thereof, and
(B) at least one further active compound selected from the group consisting of prothioconazole, trifloxystrobin and bixafen.

2. The composition according to claim 1, wherein the at least one compound of formula (I) is the compound of formula (Ia)

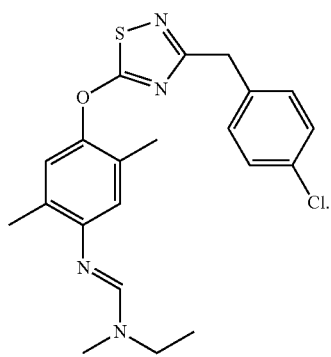

3. The composition according to claim 1 wherein the at least one further active compound (B) is prothioconazole.

4. The composition according to claim 1 wherein the at least one further active compound (B) is trifloxystrobin.

5. The composition according to claim 1 wherein the at least one further active compound (B) is bixafen.

6. The composition according to claim 1 wherein the weight ratio of (A) to (B) is from 1:100 to 100:1.

7. The composition according to claim 1 further comprising adjuvants, solvents, carrier, surfactants or extenders.

8. The composition according to claim 1 further comprising seed.

9. A method for controlling phytopathogenic fungi of plants or reducing mycotoxin contamination of plants or plant parts comprising applying to a seed, a plant, a fruit of the plant, soil in which the plant is growing or to soil from which the plant is grown:
(A) at least one compound according to formula (I)

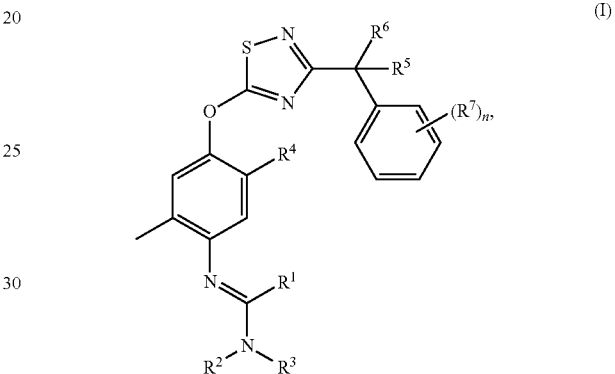

wherein
$R^1$ is selected from the group consisting of hydrogen, mercapto (—SH), and methyl;
$R^2$ is selected from the group consisting of methyl and ethyl;
$R^3$ is selected from the group consisting of methyl, ethyl, and isopropyl;
or alternatively $R^2$ and $R^3$ form, together with the N-atom to which they are attached, a piperidyl, a pyrrolidyl or a 2,6-dimethylmorpholinyl ring;
$R^4$ is selected from the group consisting of chlorine, fluorine, trifluoromethyl, difluoromethyl and methyl;
$R^5$ and $R^6$ independently from each other, are selected from the group consisting of hydrogen, methyl and ethyl; or form, together with the C-atom to which they are attached, a cyclopropyl ring;
$R^7$ is selected from the group consisting of chlorine, tert-butyl, methoxy, ethoxy, trimethylsilyl and triethylsilyl;
n is 1
or salts or stereoisomers thereof, and
(B) at least one further active compound selected from the group consisting of prothioconazole, trifloxystrobin and bixafen.

10. The method according to claim 9 comprising applying (A) and (B) simultaneously or sequentially.

11. The method according to claim 9 wherein (A) and (B) are applied as foliar treatment to the plant.

12. The method according to claim 11 wherein (A) and (B) are applied at a rate of from 0.1 to 10 kg/ha.

13. The method according to claim 9 wherein (A) and (B) are applied to the soil in which the plants are growing or to the soil from which the plants are grown.

14. The method according to claim 13 wherein (A) and (B) are applied at a rate of from 0.1 to 10 kg/ha.

15. The method according to claim 9 wherein (A) and (B) are applied to the seed.

16. The method according to claim 15 wherein the seed is seed of a transgenic plant.

17. The method according to claim 15 wherein (A) and (B) are applied to the seed at a rate of from 2 to 200 g/100 kg of seed.

18. The method according to claim 9 wherein the at least one further active compound (B) is prothioconazole.

19. The method according to claim 9 wherein the at least one further active compound (B) is trifloxystrobin.

20. The method according to claim 9 wherein the at least one further active compound (B) is bixafen.

* * * * *